US012429405B2

(12) United States Patent
Ren et al.

(10) Patent No.: US 12,429,405 B2
(45) Date of Patent: Sep. 30, 2025

(54) SEQUENTIAL DIGESTION OF POLYPEPTIDES FOR MASS SPECTROMETRIC ANALYSIS

(71) Applicant: Amgen Inc., Thousand Oaks, CA (US)

(72) Inventors: Da Ren, Thousand Oaks, CA (US); Melissa Sato, Santa Monica, CA (US)

(73) Assignee: AMGEN INC., Thousand Oaks, CA (US)

( * ) Notice: Subject to any disclaimer, the term of this patent is extended or adjusted under 35 U.S.C. 154(b) by 1179 days.

(21) Appl. No.: 16/980,344

(22) PCT Filed: Mar. 13, 2019

(86) PCT No.: PCT/US2019/022126
§ 371 (c)(1),
(2) Date: Sep. 11, 2020

(87) PCT Pub. No.: WO2019/178280
PCT Pub. Date: Sep. 19, 2019

(65) Prior Publication Data
US 2021/0255075 A1    Aug. 19, 2021

Related U.S. Application Data

(60) Provisional application No. 62/642,549, filed on Mar. 13, 2018.

(51) Int. Cl.
*G01N 1/00*    (2006.01)
*G01N 1/40*    (2006.01)
(Continued)

(52) U.S. Cl.
CPC .............. *G01N 1/4044* (2013.01); *G01N 1/40* (2013.01); *G01N 30/00* (2013.01); *G01N 30/04* (2013.01);
(Continued)

(58) Field of Classification Search
CPC ........ G01N 1/4044; G01N 1/40; G01N 30/00; G01N 30/04; G01N 30/06; G01N 30/14;
(Continued)

(56) References Cited

U.S. PATENT DOCUMENTS 7,153,507 B2    12/2006    Van De Winkel
7,592,429 B2    9/2009    Paszty
(Continued)

FOREIGN PATENT DOCUMENTS

GB    2440050 B    10/2011
WO    2017136753 A1    8/2017

OTHER PUBLICATIONS

Swaney, Danielle L., Craig D. Wenger, and Joshua J. Coon. "Value of using multiple proteases for large-scale mass spectrometry-based proteomics." Journal of proteome research 9.3 (2010): 1323-1329. (Year: 2010).*

(Continued)

*Primary Examiner* — Jyoti Nagpaul
(74) *Attorney, Agent, or Firm* — Jonathan M. Dermott

(57) ABSTRACT

The disclosed methods are directed to preparing polypeptides for multi-attribute analysis. The polypeptides are optionally denatured, reduced, and/or alkylated before being subjected to a first digestion. Following the first digestion the large and small fragments resulting from the digestion are separated from each other. A second digestion is then performed on the larger of the fragments. All of the fragments from the two digestions are then analyzed chromatographically, electrophoretically, or spectrometrically, or a combination of these methods. The methods are especially useful for the preparation of therapeutic polypeptides for analysis, especially those that are not easily cleaved.

32 Claims, 2 Drawing Sheets

(51) Int. Cl.
| | |
|---|---|
| *G01N 30/00* | (2006.01) |
| *G01N 30/04* | (2006.01) |
| *G01N 30/06* | (2006.01) |
| *G01N 30/14* | (2006.01) |
| *G01N 33/68* | (2006.01) |
| G01N 30/02 | (2006.01) |

(52) U.S. Cl.
CPC .............. *G01N 30/06* (2013.01); *G01N 30/14* (2013.01); *G01N 33/6848* (2013.01); *C12Y 304/21004* (2013.01); *C12Y 304/21037* (2013.01); *G01N 2030/027* (2013.01); *G01N 2030/067* (2013.01)

(58) Field of Classification Search
CPC ......... G01N 33/6848; G01N 2030/027; G01N 2030/067; G01N 30/7233; G01N 2030/8831; C12Y 304/21004; C12Y 304/21037; C07K 1/12; C12N 9/50; C12N 9/6448; C12P 21/06
See application file for complete search history.

(56) References Cited

U.S. PATENT DOCUMENTS

| | | | |
|---|---|---|---|
| 7,906,625 B2 | 3/2011 | Shen | |
| 7,982,016 B2 | 7/2011 | Comeau | |
| 8,080,243 B2 | 12/2011 | Liang | |
| 8,715,663 B2 | 5/2014 | Paszty | |
| 2002/0076817 A1* | 6/2002 | Figeys | G01N 33/6851 436/6 |
| 2006/0105415 A1* | 5/2006 | Miyagi | C12Q 1/37 435/68.1 |
| 2010/0203565 A1* | 8/2010 | Broberg | G01N 33/6848 435/23 |
| 2011/0111513 A1* | 5/2011 | Baumann | G01N 33/6848 250/288 |
| 2011/0151493 A1* | 6/2011 | Cockrill | G01N 33/6824 435/23 |
| 2018/0052169 A1* | 2/2018 | Kraus | G01N 33/57496 |

OTHER PUBLICATIONS

Crimmins et al., "Chemical Cleavage of Proteins in Solution" In Current Protocols in Protein Science. John Wiley & Sons, Inc (2001).
Doucet et al., "Broad Coverage Identification of Multiple Proteolytic Cleavage Site Sequences in Complex High Molecular Weight Proteins Using Quantitative Proteomics as a Complement to Edman Sequencing," Mol. Cell. Proteomics, 10(5):1074 (2011).
Gunzler et al., "Handbook of analytical techniques" TOC, Wiley-VCH, Weinheim, Germany. pp. 1198 (2001).
International Preliminary Report on Patentability, European Patent Office PCT/US2019/022126, dated Sep. 15, 2020.
International Search Report and Written Opinion of the International Search Authority, European Patent Office PCT/US2019/022126, dated Jun. 28, 2019.
Janoff et al., "Mediators of Inflammation in Leukocyte Lysosomes—Elastinolytic Activity in Granules of Human Polymorphonuclear Leukocytes," Dept. of Pathology, NY Univ. School of Medicine, 1137-1155 (1968).
Kurien et al., "Protein electrophoresis: Methods and protocols," TOC, Humana Press ; Springer, New York. xiv, pp. 648 (2012).
Li et a., "Chemical Cleavage at Aspartyl Residues for Protein Identification,". Analytical Chemistry, vol. 73 pp. 5395-5402 (2001).
Lord, G.A. "Capillary electrophoresis of proteins and peptides,"Methods in Molecular Biology, vol. 276 (Issue 18) 875 (2004).
Nowicka-Jankowska, T. "Analytical visible and ultraviolet spectrometry." Elsevier Science Pub. Coxvi, pp. 690 (1986).
Pontius et al., "UniGene: a unified view of the transcriptome," In The NCBI Handbook. National Center for Biotechnology Information, Bethesda (MD) (2003).
Rawlings et al., MEROPS: The Database of Proteolytic Enzymes, Their Substrates and Inhibitors, Nucleic Acids Research 42:503-509 (2014).
Rohani et al., "A Refined One-Filtration Method for Aqueous Based Nanofiltration and Ultrafiltration Membrane Molecular Weight Cut-Off Determination Using Polyethylene Glycols," Journal of Membrane Science 382:278-290 (2011).
Rubakhin et al., "Mass spectrometry imaging : principles and protocols," TOC Humana Press, New York. pp. 487 (2010).
Sinha et al., "Primary structure of human neutrophil elastase". Proc Natl Acad Sci USA. vol. 84 pp. 2228-2232. (1987).
Stein et al., Catalysis by Human Leukocyte Elastase: Mechanistic Insights into Specificity Requirements, Biochemistry 26:1301-1305 (1987).
Tanabe et al., "Asparagine-selective cleavage of peptide bonds through hypervalent iodine-mediated Hofmann rearrangement in neutral aqueous solution," Chemical Science, vol. 5 pp. 2747-2753 (2014).
Tanford, Charles, Protein Denaturation, Dept. of Biochemistry, Duke University Medical Center, Durham, N.C. 121-282 (1968).
The UniProt, C. 2017. UniProt: the universal protein knowledgebase. Nucleic acids research. 45:D158-D169.
Tran et al., "Addressing Trypsin Bias in Large Scale (Phospho)proteome Analysis by Size Exclusion Chromatography and Secondary Digestion of Large Post-Trypsin Peptides," Journal of Proteome Research, vol. 10 (Issue 2) pp. 800-811 (2011).
Unspecified Table 2. List of proteases commonly used for fragmenting proteins. Cold Spring Harbor Protocols. 2007: pdb.tab2ip13. (2007).
Wisniewski et al., "Universal sample preparation method for proteome analysis" Nature methods,. vol. 6 pp. 359-362 (2009).

* cited by examiner

SEQUENTIAL DIGESTION OF POLYPEPTIDES FOR MASS SPECTROMETRIC ANALYSIS

CROSS-REFERENCE TO RELATED APPLICATIONS

This application is a national stage application under 35 U.S.C § 371 of International Application No. PCT/US2019/022126, filed on Mar. 13, 2019, which claims the benefit of U.S. Provisional Patent Application No. 62/642,549, filed on Mar. 13, 2018, all of which are incorporated herein by reference in their entireties.

FIELD

The presented subject matter relates to the field of polypeptide analysis. Specifically, the presented subject matter relates to the preparation of samples for the detection of polypeptides comprised therein, such as therapeutic polypeptides. The disclosed methods use sequential digestion and separation in the preparation of the polypeptides.

BACKGROUND

Multi-attribute method (MAM) relies on enzymatic digest of molecules followed by mass spectrometry-based characterization and quantitation of attributes of interest. Modifications in the complementary-determining regions (CDRs) are of particular concern because they may impact potency and/or safety of the molecule. The present invention describes a novel enzymatic digestion approach using multiple enzymes. Enzymatic digestions cleave proteins on specific amino acid residues. Due to the uneven distribution of these specific cleavable residues in proteins, single enzyme digestion can produce large peptides that are challenging to analyze by MAM and other analytical technologies. To address this issue, a second enzyme is normally used. Conventionally, the second enzyme is used together with the first enzyme at the same time, or used independently. The disadvantages for conventional multiple enzyme digestion is that it either ends up with a complicated digest with too many peaks, or multiple enzymatic digestions need to be analyzed separately. The method described herein uses multiple enzymes to digest proteins in a sequential fashion, which eliminates the interference among various enzymes and the end product is a single clean digest with the number of peptide peaks that is close to that of single enzyme digestion. This method is friendly to MAM and other analytical technologies such as LC/UV peptide mapping method.

SUMMARY OF THE INVENTION

The present application is directed to a method of preparing a polypeptide for analysis, comprising:
cleaving the polypeptide in a first digestion, wherein the cleaving produces at least two fragments of the polypeptide; separating the at least two fragments from each other to produce a first large peptide fragment-containing solution and a first small peptide fragment-containing solution;
a. cleaving the large peptide fragments of the first large peptide fragment-containing solution in a second digestion, wherein at least one of the large peptide fragments of the first large peptide fragment-containing solution is cleaved to produce at least two fragments of the large peptide fragments of the first large peptide fragment-containing solution;
b. analyzing the digested solution of c. and the small peptide fragment-containing solution of b.

In one embodiment, the digested solution of c. and the small peptide fragment-containing solution of b. are combined before analysis.

In another aspect the present invention is directed to a method of preparing a polypeptide for analysis, comprising:
cleaving the polypeptide in a first digestion, wherein the cleaving produces at least two fragments of the polypeptide; separating the at least two fragments from each other to produce a first large peptide fragment-containing solution and a first small peptide fragment-containing solution;
a. cleaving the large peptide fragments of the first large peptide fragment-containing solution in a second digestion, wherein at least one of the large peptide fragments of the first large peptide fragment-containing solution is cleaved to produce at least two fragments of the large peptide fragments of the first large peptide fragment-containing solution;
b. separating the at least two fragments of the large peptide fragments from each other to produce a second large peptide fragment-containing solution and a second small peptide fragment-containing solution;
c. cleaving the large peptide fragments of the second large peptide fragment-containing solution in a third digestion, wherein at least one of the large peptide fragments of the second large peptide fragment-containing solution is cleaved to produce at least two fragments of the large peptide fragments of the second large peptide fragment-containing solution;
d. analyzing the digested solution of c., the first small peptide fragment-containing solution of b., and the second small peptide fragment-containing solution of d.

In one embodiment, the digested solution of c., the first small peptide fragment-containing solution of b., and the second small peptide fragment-containing solution of d. are combined before analysis.

In certain embodiments, the cleaving of the polypeptide in the first digestion comprises proteolytic or chemical cleavage. In one embodiment, the cleaving is proteolytic cleavage accomplished by a protease. In certain embodiments, the protease is selected from the group consisting of neutrophil elastase, trypsin, endoproteinase Glu-C, endoproteinase Arg-C, pepsin, chymotrypsin, chymotrypsin B, Lys-N protease, Lys-C protease, Glu-C protease, Asp-N protease, pancreatopeptidase, carboxypeptidase A, carboxypeptidase B, proteinase K, and thermolysin, and combinations thereof.

In another embodiment, the cleaving is chemical cleavage accomplished by a chemical. In certain embodiments the chemical is selected from the group consisting of cyanogen bromide, 2-Nitro-5-thiocyanobenzoate, hydroxlamine, and BNPS-skatole, and combinations thereof.

In certain embodiments, the polypeptide is denatured before cleaving the polypeptide in the sample in the first digestion. In certain embodiments, the polypeptide is alkylated before cleaving the polypeptide in the sample in the first digestion. In certain embodiments, the polypeptide is denatured and either alkylated or reduced before cleaving the polypeptide in the sample in the first digestion.

In one embodiment, the polypeptide is denatured, reduced, and alkylated before cleaving the polypeptide in the sample in the first digestion.

In one embodiment, the cleaving of the polypeptide in the second digestion comprises proteolytic cleavage accomplished by a protease.

In certain embodiments, the protease of the second digestion is selected from the group consisting of neutrophil elastase, trypsin, endoproteinase Glu-C, endoproteinase Arg-C, pepsin, chymotrypsin, chymotrypsin B, Lys-N protease, Lys-C protease, Glu-C protease, Asp-N protease, pancreatopeptidase, carboxypeptidase A, carboxypeptidase B, proteinase K, and thermolysin, and combinations thereof; wherein the protease is different than the protease used for cleaving the polypeptide in the first digestion. In one embodiment, the protease is neutrophil elastase. In one embodiment, the neutrophil elastase is human neutrophil elastase (EC 3.4.21.37).

In certain embodiments, the analyzing comprises at least one technique selected from the group consisting of chromatography, electrophoresis, spectrometry, and combinations thereof.

In one embodiment, the technique for analyzing the sample comprises:
chromatography and is selected from the group consisting of gas chromatography, liquid chromatography, high performance liquid chromatography, ultra-performance liquid chromatography, size-exclusion chromatography, ion-exchange chromatography, affinity chromatography, expanded bed adsorption chromatography, reverse-phase chromatography, hydrophobic interaction chromatography, and combinations thereof;
a. electrophoresis and is selected from the group consisting of gel electrophoresis, free-flow electrophoresis, electrofocusing, isotachophoresis, affinity electrophoresis, immunoelectrophoresis, counterelectrophoresis, and capillary electrophoresis, capillary zone electrophoresis, and combinations thereof; or
b. spectrometry and is selected from the group consisting of mass spectrometry, ultraviolet spectrometry, visible light spectrometry, fluorescent spectrometry, and ultraviolet-visible light spectrometry, and combinations thereof.

In one embodiment, the technique comprises liquid chromatography-mass spectrometry. In one embodiment, the technique comprises capillary zone electrophoresis coupled to mass spectrometry. In one embodiment, the cleaving of the polypeptide in the third digestion comprises proteolytic cleavage accomplished by a protease. In one embodiment, the protease of the third digestion is selected from the group consisting of neutrophil elastase, trypsin, endoproteinase Glu-C, endoproteinase Arg-C, pepsin, chymotrypsin, chymotrypsin B, Lys-N protease, Lys-C protease, Glu-C protease, Asp-N protease, pancreatopeptidase, carboxypeptidase A, carboxypeptidase B, proteinase K, and thermolysin, and combinations thereof; wherein the protease is different than the protease used for cleaving the polypeptide in the first digestion and different than the protease used for cleaving the polypeptide in the second digestion.

In one aspect the present invention is directed to a method of preparing a polypeptide for analysis, comprising:
a. denaturing, reducing, and alkylating the polypeptide;
b. digesting the polypeptide with trypsin to produce large trypsin-cleaved polypeptide fragments and small trypsin-cleaved polypeptide fragments;
c. separating the large and small trypsin-cleaved polypeptide fragments into a first aliquot and a second aliquot;
d. digesting the large trypsin-cleaved polypeptide fragments of the first aliquot with neutrophil elastase;
e. combining the first aliquot and second aliquot at about a 1:1 ratio; and
f. analyzing the combined aliquots of step (e).

In one embodiment, the at least two fragments of step a. are separated using a molecular weight cutoff filter. In one embodiment, the molecular cutoff of the filter is 30 kDa.

In one embodiment, the polypeptide is a therapeutic polypeptide. In one embodiment, the therapeutic polypeptide is selected from the group consisting of an antibody or antigen-binding fragment thereof, a derivative of an antibody or antibody fragment, and a fusion polypeptide.

In certain embodiments, the therapeutic polypeptide is selected from the group consisting of infliximab, bevacizumab, cetuximab, ranibizumab, palivizumab, abagovomab, abciximab, actoxumab, adalimumab, afelimomab, afutuzumab, alacizumab, alacizumab pegol, ald518, alemtuzumab, alirocumab, altumomab, amatuximab, anatumomab mafenatox, anrukinzumab, apolizumab, arcitumomab, aselizumab, altinumab, atlizumab, atorolimiumab, tocilizumab, bapineuzumab, basiliximab, bavituximab, bectumomab, belimumab, benralizumab, bertilimumab, besilesomab, bevacizumab, bezlotoxumab, biciromab, bivatuzumab, bivatuzumab mertansine, blinatumomab, blosozumab, brentuximab vedotin, briakinumab, brodalumab, canakinumab, cantuzumab mertansine, cantuzumab mertansine, caplacizumab, capromab pendetide, carlumab, catumaxomab, cc49, cedelizumab, certolizumab pegol, cetuximab, citatuzumab bogatox, cixutumumab, clazakizumab, clenoliximab, clivatuzumab tetraxetan, conatumumab, crenezumab, cr6261, dacetuzumab, daclizumab, dalotuzumab, daratumumab, demcizumab, denosumab, detumomab, dorlimomab aritox, drozitumab, duligotumab, dupilumab, ecromeximab, eculizumab, edobacomab, edrecolomab, efalizumab, efungumab, elotuzumab, elsilimomab, enavatuzumab, enlimomab pegol, enokizumab, enoticumab, ensituximab, epitumomab cituxetan, epratuzumab, erenumab, erlizumab, ertumaxomab, etaracizumab, etrolizumab, evolocumab, exbivirumab, fanolesomab, faralimomab, farletuzumab, fasinumab, fbta05, felvizumab, fezakinumab, ficlatuzumab, figitumumab, flanvotumab, fontolizumab, foralumab, foravirumab, fresolimumab, fulranumab, futuximab, galiximab, ganitumab, gantenerumab, gavilimomab, gemtuzumab ozogamicin, gevokizumab, girentuximab, glembatumumab vedotin, golimumab, gomiliximab, gs6624, ibalizumab, ibritumomab tiuxetan, icrucumab, igovomab, imciromab, imgatuzumab, inclacumab, indatuximab ravtansine, infliximab, intetumumab, inolimomab, inotuzumab ozogamicin, ipilimumab, iratumumab, itolizumab, ixekizumab, keliximab, labetuzumab, lebrikizumab, lemalesomab, lerdelimumab, lexatumumab, libivirumab, ligelizumab, lintuzumab, lirilumab, lorvotuzumab mertansine, lucatumumab, lumiliximab, mapatumumab, maslimomab, mavrilimumab, matuzumab, mepolizumab, metelimumab, milatuzumab, minretumomab, mitumomab, mogamulizumab, morolimumab, motavizumab, moxetumomab pasudotox, muromonab-cd3, nacolomab tafenatox, namilumab, naptumomab estafenatox, narnatumab, natalizumab, nebacumab, necitumumab, nerelimomab, nesvacumab, nimotuzumab, nivolumab, nofetumomab merpentan, ocaratuzumab, ocrelizumab, odulimomab, ofatumumab, olaratumab, olokizumab, omalizumab, onartuzumab, oportuzumab monatox, oregovomab, orticumab, otelixizumab, oxelumab, ozanezumab, ozoralizumab, pagibaximab, palivizumab, panitumumab, panobacumab, parsatuzumab, pascolizumab, pateclizumab, patritumab, pemtumomab, perakizumab, pertuzumab, pexelizumab, pidilizumab, pintumomab, placulumab, ponezumab, priliximab, pritumumab, PRO 140, quilizumab, racotumomab, radretumab, rafivirumab, ramucirumab, ranibizumab, raxibacumab, regavirumab, reslizumab, rilotumumab, rituximab, robatumumab, roledumab, romosozumab, rontalizumab, rovelizumab, ruplizumab, samalizumab, sarilumab, satumomab pendetide, secukinumab, sevirumab, sibrotuzumab, sifalimumab, siltuximab, simtuzumab, siplizumab, sirukumab, solanezumab, solitomab, sonepcizumab, sontuzumab, stamulumab, sulesomab, suvizumab, tabalumab, tacatuzumab tetraxetan, tadocizumab, talizumab, tanezumab, taplitumomab paptox, tefibazumab, telimomab aritox, tenatumomab, tefibazumab, teneliximab, teplizumab, teprotumumab, tezepelumab, TGN1412, tremelimumab, ticilimumab, tildrakizumab, tigatuzumab, TNX-650, tocilizumab, toralizumab, tositumomab, tralokinumab, trastuzumab, TRBS07, tregalizumab, tucotuzumab celmoleukin, tuvirumab, ublituximab, urelumab, urtoxazumab, ustekinumab, vapaliximab, vatelizumab, vedolizumab, veltuzumab, vepalimomab, vesencumab, visilizumab, volociximab, vorsetuzumab mafodotin, votumumab, zalutumumab, zanolimumab, zatuximab, ziralimumab, zolimomab aritox, a glycoprotein, CD polypeptide, a HER receptor polypeptide, a cell adhesion polypeptide, a growth factor polypeptide, an insulin polypeptide, an insulin-related polypeptide, a coagulation polypeptide, a coagulation-related polypeptide, albumin, IgE, a blood group antigen, a colony stimulating factor, a receptor, a neurotrophic factor, an interferon, an interleukin, a viral antigen, a lipoprotein, calcitonin, glucagon, atrial natriuretic factor, lung surfactant, tumor necrosis factor-alpha and -beta, enkephalinase, mouse gonadotropin-associated peptide, DNAse, inhibin, activing, an integrin, protein A, protein D, a rheumatoid factor, an immunotoxin, a bone morphogenetic protein, a superoxide dismutase, a surface membrane polypeptide, a decay accelerating factor, an AIDS envelope, a transport polypeptide, a homing receptor, an addressin, a regulatory polypeptide, an immunoadhesin, a myostatin, a TALL polypeptide, an amyloid polypeptide, a thymic stromal lymphopoietin, a RANK ligand, a c-kit polypeptide, a TNF receptor, and an angiopoietin, the antibodies shown in Table 7 and biologically active fragments, analogs or variants thereof.

In one embodiment, the therapeutic polypeptide is a bi-specific T-cell engager molecule.

In certain embodiments, the methods can be accomplished at least in part by automation. In certain embodiments, the addition and exchange of solutions is handled by an automated liquid handling device or robot.

DETAILED DESCRIPTION

Protein characterization is crucial throughout the lifecycle of therapeutic protein manufacturing. Due to the large size and complexity proteins, analysis of intact proteins provides limited information of the molecule. Enzymatic digestion is commonly used to break down proteins into smaller peptide for the ease of analysis. Single enzyme digestions can generate large peptide fragments that pose challenges for peptide mapping type of analysis. The disadvantages for conventional multiple enzyme digestion are that it either ends up with a complicated digest with too many peaks, or the multiple enzymatic digestions need to be analyzed separately.

The sequential digestion method described in this invention disclosure uses a divide and conquer strategy. Following an initial digestion, molecular weight cutoff filters can be used to separate the high molecular weight peptides from their low molecular weight counterparts. Subsequently, only the high molecular weight peptides are subjected to a 2nd enzyme digestion, which eliminates the complexity of mixing two full enzymatic digestions. After the second enzyme digestion, all the peptides can be mixed together to generate one peptide map, this makes it easy for MAM and other analytical methods to analyze the sample. More importantly, this method avoids quantitation of the same product attributes using multiple peptides, which is an issue for other multiple enzyme digestions.

Figure 1:
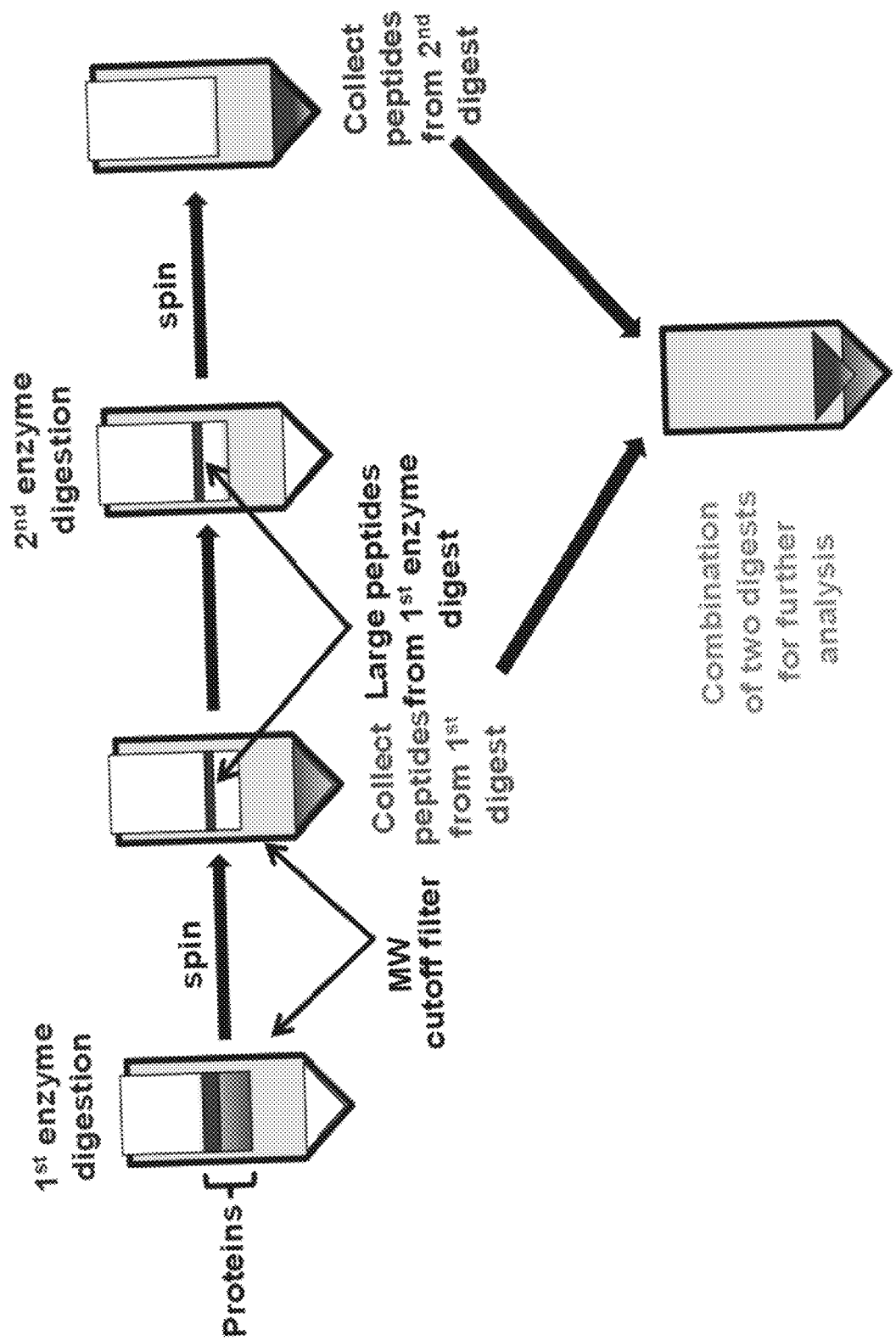
FIG. 1 shows an Illustration of Sequential Enzymatic Digestion Workflow.
Figure 2:
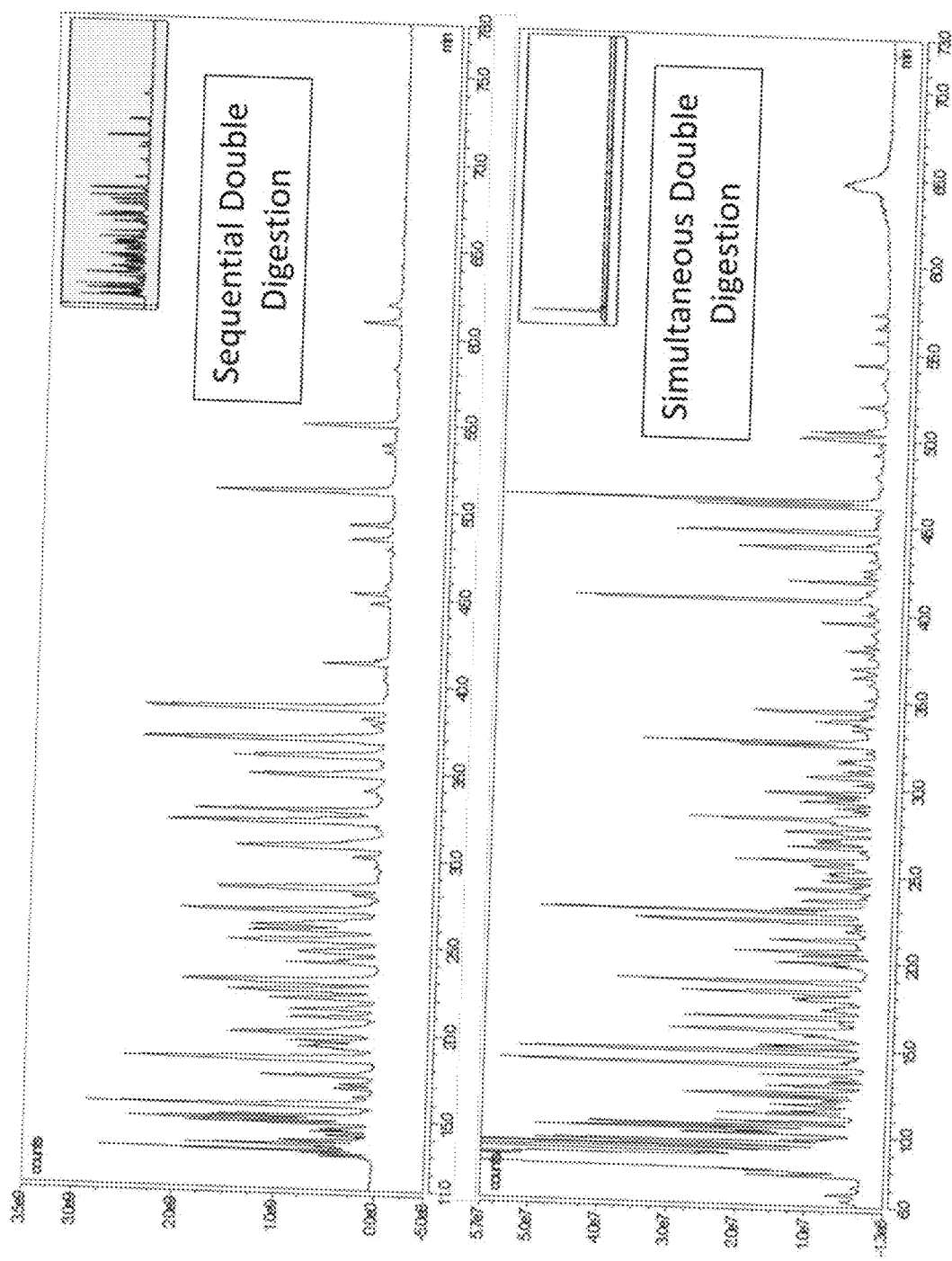
FIG. 2 shows a Comparison between sequential digestion and double digestion

As illustrated in FIG. 1, after the 1st enzymatic digestion, a molecular weight cutoff filter is used to separate the small peptides and large peptides. Normally this separation is achieved by centrifugation, but can be gravity separated when a proper filter is used. The small peptides below the molecular weight cutoff are collected after separation, and the large peptides are trapped on top of the filter, which are subsequently further digested with the 2nd enzyme. After the 2nd enzymatic digestion, the large peptides will be cleaved into smaller peptides which are below the molecular weight cutoff and can be collected after spinning down. The digests from the 1st and the 2nd digestion are mixed together and only one peptide map needs to be analyzed using MAM or other technologies. The process can be repeated N times and the digests can be mixed together to produce one peptide map after the Nth digestion.

This methodology can be used in any modality of therapeutic proteins including but not limited to mAbs, BiTEs, and Fc Fusion proteins.

Definitions

Both the foregoing general description and the following detailed description are exemplary and explanatory only and are not restrictive. The use of the singular includes the plural unless specifically stated otherwise. The use of "or" means "and/or" unless stated otherwise. The use of the term "including," as well as other forms, such as "includes" and "included," is not limiting. Terms such as "element" or "component" encompass both elements and components comprising one unit and elements and components that comprise more than one subunit unless specifically stated otherwise. The use of the term "portion" can include part of a moiety or the entire moiety. When a numerical range is mentioned, e.g., 1-5, all intervening values are explicitly included, such as 1, 2, 3, 4, and 5, as well as fractions thereof, such as 1.5, 2.2, 3.4, and 4.1.

"About" or "~" means, when modifying a quantity (e.g., "about" 3 mM), that variation around the modified quantity can occur. These variations can occur by a variety of means, such as typical measuring and handling procedures, inadvertent errors, ingredient purity, and the like.

"Comprising" and "comprises" are intended to mean that methods include the listed elements but do not exclude other unlisted elements. The terms "consisting essentially of" and "consists essentially of," when used in the disclosed methods include the listed elements, exclude unlisted elements that alter the basic nature of the method, but do not exclude other unlisted elements. The terms "consisting of" and "consists of" when used to define methods exclude substantial method steps. Embodiments defined by each of these transition terms are within the scope of this disclosure.

"Coupled" means associated directly as well as indirectly. For example, a device or process can be directly associated with another device or process, or these devices and/or processes can be indirectly associated with each other, e.g., via another device or process.

"Protein", "peptide", and "polypeptide" are used interchangeably to mean a chain of amino acids wherein each amino acid is connected to the next by a peptide bond.

"Denaturation," "denaturing," "denature," and the like means a process in which polypeptides lose at least partially the quaternary structure, tertiary structure, and secondary structure that are found in the polypeptides in their native states by applying an external stress or reagent (i.e., a denaturant).

"Denaturant" means any substance, composition, energy, or condition that can denature a polypeptide. Examples of denaturants include a strong acid or base, an inorganic salt, an organic solvent, radiation, a chaotropic agent, or heat, or combinations of these.

"Denatured polypeptide," "denatured protein," and the like means a polypeptide that has its secondary, tertiary, and/or quaternary structure changed from the native polypeptide. A polypeptide can be fully denatured or partially denatured. A "non-denatured polypeptide" or "non-denatured protein" (and similar terms) means a polypeptide that has maintained its secondary, tertiary, and as applicable, quaternary structure. A "native polypeptide" or "native protein" (and the like) refers to a polypeptide as found in nature and has any primary reference sequence described in the UniProt Knowledgebase database (The UniProt, 2017) or the UniGene database (Pontius et al., 2003).

"Reduced polypeptide" or "reduced protein" (and similar terms) means a polypeptide in which at least one of its interchain or intrachain disulfide bonds is broken. Such bonds can form between reduced thiol groups, such as those available on cysteine residues.

"Alkylated polypeptide" or "alkylated protein" (and the like) means a polypeptide to which an alkyl group has been transferred. Pragmatically, polypeptides are often alkylated on thiol groups (such as available on cysteine residues) to prevent reduced thiols from forming, or reforming after reduction, disulfide bonds or bridges.

"Digestion" and the like, in the context of polypeptides, means the fragmenting of a polypeptide into two or more fragments, which fragmentation is mediated by another substance, chemical, or enzyme.

"Proteolytic cleavage," "proteolytic digestion," and the like means the cleaving of a polypeptide by breaking the peptide bonds in a polypeptide, thus producing fragments. Proteolytic cleavage can be mediated by enzymes.

"Protease," "peptidase," "proteolytic cleavage enzyme," and the like means an enzyme and means a polypeptide or fragment thereof that catalyzes hydrolysis of peptide bonds. Proteases include variants of an amino acid sequences of known proteases that catalyze peptide bond hydrolysis, even wherein such catalyzing activity is reduced in the variant.

Enzyme catalyzed reactions are classified according to the Enzyme Commission numbering system. Because proteases catalyze peptide bond hydrolysis, they are classified in class EC 3.4, which includes, EC 3.4.11 Aminopeptidases, EC 3.4.13 Dipeptidases, EC 3.4.14 Dipeptidyl peptidases and tripeptidyl peptidases, EC 3.4.15 Peptidyl dipeptidases, EC 3.4.16 Serine type carboxypeptidases, EC 3.4.17 Metallocarboxypeptidases, EC 3.4.18 Cysteine type carboxypeptidases, EC 3.4.19 Omega peptidases, EC 3.4.21: Serine proteases, EC 3.4.22 Cysteine proteases, EC 3.4.23 Aspartic endopeptidases, EC 3.4.24: Metallopeptidases, EC 3.4.25 Threonine endopeptidases, EC 3.4.99 Endopeptidases of unknown catalytic mechanism. Specific examples of proteases include trypsin (EC 3.4.21.4), endoproteinase Asp-N (EC 3.4.24.33), and endoproteinase Glu-C (EC 3.4.21.19).

Elastases are proteases that (except for those classified as EC 3.4.21.70) hydrolyze elastin, an elastic fiber polypeptide of the extracellular matrix. There are eight human genes that encode elastases (Table 1):

TABLE 1

The Human Elastases

| Family | Gene | Name | EC number | Preferential cleavage |
|---|---|---|---|---|
| Neutrophil | ELANE (ELA2) | Neutrophil elastase (elastase 2) | 3.4.21.37 | Val-\|-Xaa; Ala-\|-Xaa; Thr-\|-Xaa; Ile-\|-Xaa; Leu-\|-Xaa |
| Chymotrypsin | CTRC (ELA4) | Chymotrypsin C (cadlecrin) (elastase 4) | 3.4.21.2 | Leu-\|-Xaa; Tyr-\|-Xaa; Phe-\|-Xaa; Met-\|-Xaa; Trp-\|-Xaa; Gln-\|-Xaa; Asn-\|-Xaa |
| Chymotrypsin-like | CELA1 (ELA1) | Chymotrypsin-like elastase family, member 1 (pancreatic elastase 1) | 3.4.21.36 | Ala-\|-Xaa |
| | CELA2A (ELA2A) | Chymotrypsin-like elastase family, member 2A (pancreatic elastase 2A) | 3.4.21.71 | Leu-\|-Xaa Met-\|-Xaa Phe-\|-Xaa |
| | CELA2B (ELA2B) | Chymotrypsin-like elastase family, member 2B (pancreatic elastase 2B) | 3.4.21.71 | Leu-\|-Xaa Met-\|-Xaa Phe-\|-Xaa |
| | CELA3A (ELA3A) | Chymotrypsin-like elastase family, member 3A (pancreatic elastase 3A) | 3.4.21.70 | Ala-\|-Xaa (Does not hydrolyze elastin) |
| | CELA3B (ELA3B) | Chymotrypsin-like elastase family, member 3B (pancreatic elastase 3B) | 3.4.21.70 | Ala-\|-Xaa (Does not hydrolyze elastin) |
| Macrophage | MMP12 (HME) | Macrophage metalloelastase (macrophage elastase) | 3.4.24.65 | Hydrolysis of soluble and insoluble elastin. Specific cleavages are also produced at 14-Ala-\|-Leu-15 and 16-Tyr-\|-Leu-17 in the B chain of insulin |

"Chemical cleavage" in the context of producing fragments of a polypeptide, means the fragmenting of the polypeptide by a chemical. A "chemical" is a non-proteinaceous substance or compound. Chemicals can be organic or inorganic.

"Molecular weight cut-off" or "MWCO" means A membrane's MWCO is a representation of membrane selectivity for solute molecules of different molecular weights (MWs), where the MW value (expressed in Daltons (Da)) is obtained from the solute molecule that gives a 90% rejection when a range of different MW solutes are filtered in the target solvent (which for most liquid based, pressure driven membrane applications is water), where rejection is defined as in Eq. (1):

$$\text{Rejection, } R(\%) = \left(1 - \frac{Cp}{Cf}\right) \times 100 \quad (1)$$

where Cp and Cf are the concentration of permeate and feed, respectively.

MWCO is determined experimentally using dextran, polyethylene glycol, and proteins of various molecular weights to rate the MWCO of membranes or filters. The rejection depends on many solute and process parameters like the type of solute, concentration, hydrodynamics, pressure, temperature and pH. MWCO measurements usually are carried out in separate experiments using different solutes, each with a certain MW.

For low range MW (approximately under 10 kDa), polyethylene glycols (PEGs), n-alkanes, and oligostyrenes can be used in solute rejection assays. For high range MW (approximately greater than 10 kDa), dextrans and sugars are often used (Rohani et al., 2011).

Methods

Disclosed herein are methods directed to digesting polypeptide in a sample with a first protease and a second protease, wherein the first protease produces at least two fragments of the polypeptide, which the at least two fragments of the polypeptide are subsequently separated from each other and the larger fragments are subsequently digested by the second protease followed by analyzing the sample after digesting with the second protease. These fragments can all be combined before analysis. The polypeptide in the sample can be denatured and/or reduced and/or alkylated before digesting with the first protease. Analysis can include chromatography, electrophoresis, spectrometry, and combinations thereof.

In some embodiments, the methods include applying the sample to a filter having a MWCO before digesting the polypeptide in the sample on the filter with the first protease, digesting the polypeptide in the sample with the second protease, and analyzing the sample. Such embodiments can further incorporate filtering steps. The MWCO filter, in some embodiments, retains a significant proportion of the polypeptide and polypeptide fragments, even though the size of these polypeptides or polypeptide fragments have a MW that is significantly smaller than the MWCO of the filter.

Method Steps

Polypeptide Denaturing

In some embodiments, the polypeptide that is prepared and analyzed according to the disclosed methods is denatured.

Polypeptides can be denatured using a variety of art-accepted techniques and denaturants. In some embodiments, multiple denaturants are used together, either simultaneously or in sequence. For example, the denaturants of SDS and heat can be combined to denature polypeptides.

Protein denaturation can be accomplished by any means that disrupts quaternary, tertiary, or secondary polypeptide structure. For example, the use of chaotropes, such as urea, and denaturing detergents (e.g., sodium dodecyl sulfate (SDS)), heat, reducing agents, and agents that inactivate reactive thiol groups to block disulfide reformation. The pH of polypeptide-containing samples can also be manipulated to encourage denaturation. These components are often used together to effectively unfold polypeptides.

Additional examples of chaotropes include, in addition to urea, n-butanol, ethanol, guanidinium chloride, lithium perchlorate, lithium acetate, magnesium chloride, phenol, 2-propanol, and thiourea. Urea is preferred in most instances.

Detergents are classified in the form of the hydrophilic group: anionic, cationic, non-ionic, and zwitterionic. Anionic and cationic detergents are more likely to be denaturing, examples of which include: SDS, sodium cholate, sodium deoxycholate, sodium glycocholate, sodium taurocholate, sodium taurodeoxycholate, N-lauroylsarcosine, lithium dodecyl sulfate (anionic) and hexadecyltrimethyl ammonium bromide (CTAB) and trimethyl (tetradecyl) ammonium bromide (TTAB) (cationic). In some cases, a zwitterionic detergent can be useful, examples include amidosulfobetaine-14 (ASB-14), amidosulfobetaine-16 (ASB-16), C7Bz0, CHAPS, CHAPSO, EMPIGEN® BB, 3-(N,N-dimethyloctylammonio) propanesulfonate inner salt (SB3-8), d (decyldimethylammonio) propanesulfonate inner salt (SB3-10), etc. Anionic detergents are preferred, with SDS being particularly preferred.

A denaturant can be heat, such as an elevated temperature at or greater than 30° C. (for most polypeptides). Denaturants include agitation. In some embodiments, low salt, including essentially or substantially or no salt can denature polypeptides.

A denaturant can be a solvent, such as ethanol or other alcohols.

Denaturing of polypeptides has been extensively studied and described; for example, see (Tanford, 1968) for further details. A person of ordinary skill in the art understands how to denature polypeptides given the nature of the polypeptide and the many denaturants from which to choose.

Reduction of Polypeptides

A reduced polypeptide is a polypeptide that is exposed to reducing conditions sufficient to reduce a reducible residue in the polypeptide structure, such as a cysteine. If the reduced polypeptide contains a thiol group, or sulfur-containing residue, then the thiol group in the reduced polypeptide is reduced. A reduced polypeptide comprising a cysteine residue has the sulfur atom of the cysteine residue reduced, which can be indicated as "—SH." A reduced polypeptide can be a disulfide bond-containing polypeptide. A disulfide bond-containing polypeptide can become a reduced polypeptide by exposure to reducing conditions that cause one or more disulfide bonds (disulfide bridges) in the disulfide bond-containing polypeptide to break.

A "reducing agent", "reductant" or "reducer" is an element or compound that loses (or donates) an electron to another chemical species in a redox chemical reaction. A reducing agent allows disulfide groups to become reactive by generating thiol (—SH) groups. Common polypeptide reducing reagents are shown in Table 2.

TABLE 2

Reducing Reagents

| Product | Notes (including alternative names and CAS entries) |
|---|---|
| 2-Mercaptoethanol | β-mercaptoethanol (BME, 2BME, 2-ME, b-mer, CAS 60-24-2) |
| 2-Mercaptoethylamine-HCl | 2-aminoethanethiol (2-MEA-HCl, cysteamine-HCl, CAS 156-57-0), selectively reduces antibody hinge-region disulfide bonds |
| Dithiothreitol | Dithiothreitol (DTT, CAS 3483-12-3) |
| TCEP-HCl | Tris (2-carboxyethyl) phosphine hydrochloride (TCEP, CAS 5961-85-3) is a thiol-free reductant for polypeptide disulfide bonds |

In some embodiments, polypeptide denaturation and reduction are carried out simultaneously. In other embodiments, the polypeptide denaturation and reduction are performed in discrete steps.

A person of ordinary skill in the art understands how to reduce polypeptides given the nature of the polypeptide and the reducing reagents from which to choose.

Alkylating a Polypeptide Comprised in a Sample

"Inactivating reactive thiol groups" means blocking free thiol groups in a polypeptide to prevent unwanted thiol-disulfide exchange reactions. Alkylating agents are substances that cause the replacement of hydrogen by an alkyl group.

Alkylation of free cysteines, often following their reduction, results in the covalent coupling of a carbamidomethyl or carboxymethyl group and prevents formation and reformation of disulfide bonds. Commonly used alkylating agents include n-ethylmaleimide (NEM), iodoacetamide (IAA) and iodoacetic acid. Examples of other suitable alkylating agents include dithiobis (2-nitro) benzoic acid; acrylamide; 4-vinylpyridine; nitrogen mustards, such as chlorambucil and cyclophosphamide; cisplatin; nitrosoureas, such as carmustine, lomustine and semustine; alkyl sulfonates, such as busulfan; ethyleneimines, such as thiotepa; and triazines, such as dacarbazine. The person skilled in the art is aware of the reagents that can be used to protect sulfhydryl groups, as well as how to use such reagents.

Polypeptide Digestion

The methods disclosed herein comprise cleaving the polypeptide to be analyzed in a sample in a first digestion, wherein the cleaving produces at least two fragments of the polypeptide. Any method of fragmenting the polypeptide can be used, provided that at least two fragments of the polypeptide are produced; furthermore, complete degradation of the polypeptide into, for example, single amino acids, is undesirable.

In such digestion step, convenient means of cleavage include using a protease. Any protease can be used, as long as such protease cleaves the polypeptide into at least two fragments.

In some embodiments, mixtures of two or more proteases can be used. In other embodiments, the first digestion can include multiple sequential digestions. For example, a first digestion is performed with a first protease, and then in a subsequent reaction, a second digestion is performed with a second protease.

Examples of useful proteases (but not at all inclusive) include trypsin, neutrophil elastase, endoproteinase Glu-C, endoproteinase Arg-C, pepsin, chymotrypsin, chymotrypsin B, Lys-N protease, Lys-C protease, Glu-C protease, Asp-N protease, pancreatopeptidase, carboxypeptidase A, carboxypeptidase B, proteinase K, and thermolysin. In some embodiments, combinations of these proteases are used. In some embodiments, trypsin alone is used.

These and other proteases, including peptide bond selectivity and E.C. numbers, are shown in Table 3, which is adapted from (Unspecified, 2007). The sources shown for each protease are exemplary only; many of these proteases are commercially available.

In some embodiments, a protein: protease ratio (w/w) of 10:1, 20:1, 25:1, 50:1, or 100:1 can be used. In some embodiments, the ratio is 20:1. In some embodiments, the protease used is at a concentration of about 100 ng/ml-1 mg/ml, or about 100 ng/ml-500 µg/ml, or about 100 ng/ml-100 µg/ml, or about 1 µg/ml-1 mg/ml, or about 1 µg/ml-500 µg/ml, or about 1 µg/ml-100 g/ml, or about 10 µg/mg-1 mg/ml, or about 10 µg/mg-500 µg/ml, or about 10 µg/mg-100 µg/ml. In some embodiments, the digestion step is for 10 minutes to 48 hours, or 30 minutes to 48 hours, or 30 minutes to 24 hours, or 30 minutes to 16 hours, or 1 hour to 48 hours, or 1 hour to 24 hours, or 1 hour to 16 hours, or 1 to 8 hours, or 1 to 6 hours, or 1 to 4 hours. In some embodiments, the digestion step is incubated at a temperature between 20° C. and 45° C., or between 20° C. and 40° C., or between 22° C. and 40° C., or between 25° C. and 37° C. In some embodiments, the digestion step is incubated at 37° C. One of skill in the art can choose appropriate conditions (buffers, incubation times, amount of protease, volumes, etc.), as in vitro protease digestion is well understood in the art.

TABLE 3

Proteases commonly used for protein fragmentation

| Protease[a] | EC No. | Peptide Bond Selectivity | Exemplary Accession No.[b] |
|---|---|---|---|
| Trypsin (bovine) | 3.4.21.4 | $P_1$-$P_1^1$-($P_1$ = Lys, Arg) | P00760[S] |
| Chymotrypsin (bovine) | 3.4.21.1 | $P_1$-$P_1^1$-($P_1$ = aromatic, $P_1^1$ = nonspecific) | P00766[S] |
| Endoproteinase Asp-N (*Pseudomonas fragi*) | 3.4.24.33 | $P_1$-Asp-(and -$P_1$-cysteic acid) | φ |
| Endoproteinase Arg-C (mouse submaxillary gland) | φ | -Arg-$P_1$- | — |
| Endoproteinase Glu-C (V8 protease) (*Staphylococcus aureus*) | 3.4.21.19 | -Glu-$P_1^1$-(and -Asp-$P_1^1$-) (2) | P04188[S] |

TABLE 3-continued

Proteases commonly used for protein fragmentation

| Protease[a] | EC No. | Peptide Bond Selectivity | Exemplary Accession No.[b] |
|---|---|---|---|
| Endoproteinase Lys-C (Lysobacter enzymogenes) | 3.4.21.50 | -Lys-$P_1^1$- | S77957[P] |
| Pepsin (porcine) | 3.4.23.1 | $P_1$-$P_1^1$-($P_1$ = hydrophob pref.) | P00791[S] |
| Thermolysin (Bacillus thermoproteolyticus) | 3.4.24.27 | $P_1$-$P_1^1$-(P1 = Leu, Phe, Ile, Val, Met, Ala) | P00800[S] |
| Elastase (porcine) (not neutrophil elastase) | 3.4.21.36 | $P_1$-$P_1^1$-($P_1$ = uncharged, nonaromatic) | P00772[S] |
| Papain (Carica papaya) | 3.4.22.2 | $P_1$-$P_1^1$-($P_1$ = Arg, Lys pref.) | P00784[S] |
| Proteinase K (Tritirachium album) | 3.4.21.64 | $P_1$-$P_1^1$-($P_1$ = aromatic, hydrophob pref.) | P06873[S] |
| Subtilisin (Bacillus subtilis) | 3.4.21.62 | $P_1$-$P_1^1$-($P_1$ = neutral/acidic pref.) | P04189[S] |
| Clostripain (endoproteinase-Arg-C) (Clostridium histolyticum) | 3.4.22.8 | -Arg-$P_1^1$-($P_1$ = Pro pref.) | P09870[S] |
| Carboxypeptidase A (bovine) | 3.4.17.1 | $P_1$-$P_1^1$-($P_1$cannot be Arg, Lys, Pro) | P00730[S] |
| Carboxypeptidase B (porcine) | 3.4.17.2 | $P_1$-$P_1^1$-($P_1$ = Lys, Arg) | P00732[S] |
| Carboxypeptidase P (Penicillium janthinellum) | φ | $P_1$-$P_1^1$-(nonspecific) | — |
| Carboxypeptidase Y (yeast) | 3.4.16.5 | $P_1$-$P_1^1$-(nonspecific) | P00729[S] |
| Cathepsin C | 3.4.14.1 | X-$P_1$-$P_1^1$-(removes amino-terminal dipeptide) | — |
| Acylamino-acid-releasing enzyme (porcine) | 3.4.19.1 | Ac-$P_1$-$P_1^1$-($P_1$ = Ser, Ala, Met pref.) | P19205[S]+ |
| Pyroglutamate aminopeptidase (bovine) | 3.4.19.3 | $P_1$-$P_1^1$-($P_1$ = 5-oxoproline or pyroglutamate) | — |

[a]Exemplary source shown in parentheses
[b]S = SwissProt; P = PIR; + = porcine sequence; φ = partial sequences of Asp-N; accession numbers: AAB35279, AAB35280, AAB35281, AAB35282

In some embodiments, the first digestion is accomplished using a chemical. Especially useful chemicals include those that cleave polypeptides in a site-specific manner. Such chemicals include cyanogen bromide (CNBr; carbononitridic bromide), which cleaves C-terminal of methionine residues; 2-nitro-5-thiocyanobenzoate (NTCB), which cleaves N-terminally of cysteine residues; asparagine-glycine dipeptides can be cleaved using hydroxlamine; formic acid, which cleaves at aspartic acid-proline (Asp-Pro) peptide bonds, and BNPS-skatole (3-bromo-3-methyl-2-(2-nitrophenyl) sulfanylindole), which cleaves C-terminal of tryptophan residues. One of skill in the art understands how to select appropriate variables, including polypeptide concentration, chemical concentration, incubation time and temperature, etc. See also, for example, (Crimmins et al., 2001; Li et al., 2001; Tanabe et al., 2014).

In some embodiments, the first digestion can include multiple sequential digestions, wherein at least one of such sequential digestions comprises using a chemical, such as CNBr, NTCB, hydroxylamine, formic acid, and BNPS-skatole. For example, a first digestion is performed with chemical that cleaves the polypeptide into at least two fragments, and then in a subsequent reaction, a second digestion is performed with a protease, or vice versa.

In the disclosed methods, a subsequent digestion is performed with the only caveat being that the first digestion and the second digestion use different chemical or proteolytic means. In some embodiments, the second digestion is performed using neutrophil elastase. The second digestion can be performed using the embodiments described for the first digestion.

Filter Selection

When choosing the appropriate MWCO for specific applications, many factors are usually considered, including sample concentration, composition, molecular shape, and operating conditions such as temperature, pressure, and cross-flow velocity. Other variables regarding the flow of molecule passage are also factored in. For example, linear molecules, high transmembrane pressure (TMP) and low sample concentration can increase molecule passage, while low temperature and membrane fouling can decrease molecule passage. Qualification methods for MWCO are not always comparable, as they vary across manufacturers. In the art, it is commonly advised to select a MWCO that is at least two times smaller than the molecular weight of the solute that is being retained. In one embodiment the MWCO is 30 kDa.

Suitable materials for the MWCO membrane are hydrophilic. Suitable hydrophilic materials include polyethersulfone, polyvinylidene difluoride, and regenerated cellulose.

Suitable cut-off filters can be obtained commercially, such as from Pall Corporation (Port Washington, NY) or Millipore, Inc (Burlington, MA).

Filtering the sample using MWCO filters can use any suitable filter method, using any suitable filter device. Filtering can take place by gravity, capillary force, or commonly centrifugation, including ultracentrifugation.

Analyzing the Sample

After the polypeptide has been digested a second time, the resulting polypeptide fragment can be analyzed by any suitable method. The proceeding discussion is not meant to limit in any way the methods that can be used to analyze the prepared polypeptides.

In general, suitable analytical methods can be chromatographic, electrophoretic, and spectrometric. Some of these methods can be combined.

One of skill in the art has access to, for example, handbooks, that facilitate the selection of appropriate analytical methods, as well as appropriate conditions to conduct those methods, including for example, (Gunzler and Williams, 2001).

Chromatographic methods are those methods that separate polypeptide fragments in a mobile phase, which phase is processed through a structure holding a stationary phase. Because the polypeptide fragments are of different sizes and compositions, each fragment has its own partition coefficient. Because of the different partition coefficients, the polypeptides are differentially retained on the stationary phase. Examples of such methods known in the art include gas chromatography, liquid chromatography, high performance liquid chromatography, ultra-performance liquid chromatography, size-exclusion chromatography, ion-exchange chromatography, affinity chromatography, expanded bed adsorption chromatography, reverse-phase chromatography, and hydrophobic interaction chromatography.

A summary of some of the known chromatographic methods is shown in Table 4.

TABLE 4

Examples of Chromatographic Methods

| Chromatographic Type | Description |
| --- | --- |
| Adsorption | Adsorbent stationary phase |
| Affinity | Based on a highly specific interaction such as that between antigen and antibody or receptor and ligand, one such substance being immobilized and acting as the sorbent |
| Column | The various solutes of a solution travel down an absorptive column where the individual components are absorbed by the stationary phase. The most strongly adsorbed component will remain near the top of the column; the other components will pass to positions farther down the column according to their affinity for the adsorbent |
| Exclusion (including gel-filtration, gel-permeation, molecular exclusion, molecular sieve gel-filtration) | Stationary phase is a gel having a closely controlled pore size. Molecules are separated based on molecular size and shape, smaller molecules being temporarily retained in the pores |
| Expanded bed adsorption (EBA) | Useful for viscous and particulate solutions. Uses for the solid phase particles that are in a fluidized state, wherein a gradient of particle size is created. |
| Gas (GC) | An inert gas moves the vapors of the materials to be separated through a column of inert material |
| Gas-liquid (GLC) | Gas chromatography where the sorbent is a nonvolatile liquid coated on a solid support |
| Gas-solid (GSC) | Gas chromatography where the sorbent is an inert porous solid |
| High-performance liquid, high-pressure liquid (HPLC). | Mobile phase is a liquid which is forced under high pressure through a column packed with a sorbent |
| Hydrophobic interaction chromatography | Matrix is substituted with hydrophobic groups (such as methyl, ethyl, propyl, octyl, or phenyl). At high salt concentrations, non-polar sidechains on polypeptide surfaces interact with the hydrophobic groups; that is, both types of groups are excluded by a polar solvent; elution accomplished with decreasing salt, increasing concentrations of detergent, and/or changes in pH. |
| Ion exchange | Stationary phase is an ion exchange resin to which are coupled either cations or anions that exchange with other cations or anions in the material passed through. |
| Paper | Paper is used for adsorption |
| Partition | The partition of the solutes occurs between two liquid phases (the original solvent and the film of solvent on an adsorption column) |
| Reverse-phase | Any liquid chromatography in which the mobile phase is significantly more polar than the stationary phase. Hydrophobic molecules in the mobile phase adsorb to the hydrophobic stationary phase; hydrophilic molecules in the mobile phase tend to elute first. |
| Thin-layer (TLC) | Chromatography through a thin layer of inert material, such as cellulose |
| Ultra-performance liquid (UPLC) | A liquid chromatographic technique that uses a solid phase with particles less than 2.5 μm (smaller than in HPLC) and has higher flow rates; pressure used is 2-3 times more than in HPLC. |

Prepared polypeptides can be analyzed also using electrophoretic methods-gel electrophoresis, free-flow electrophoresis, electrofocusing, isotachophoresis, affinity electrophoresis, immunoelectrophoresis, counterelectrophoresis, capillary electrophoresis, and capillary zone electrophoresis. Overviews and handbooks are available to one of skill in the art, such as (Kurien and Scofield, 2012; Lord, 2004).

Electrophoresis can be used to analyze charged molecules, such as polypeptides which are not at their isoelectric point, which are transported through a solvent by an electrical field. The polypeptides migrate at a rate proportional to their charge density. A polypeptide's mobility through an electric field depends on: field strength, net charge on the polypeptide, size and shape of the polypeptide, ionic strength, and properties of the matrix through which the polypeptide migrates (e.g., viscosity, pore size). Polyacrylamide and agarose are two common support matrices. These matrices serve as porous media and behave like a molecular sieve. Polyacrylamide forms supports with smaller pore sizes and is especially useful in the disclosed methods, being ideal for separating most polypeptide fragments.

Table 5 presents examples of polypeptide electrophoretic techniques.

TABLE 5

Examples of electrophoretic methods

| Technique | Description |
| --- | --- |
| Gel electrophoresis | Refers to electrophoretic techniques that use a gel as a matrix through which polypeptides travel. Many electrophoretic techniques use gels, including those based on polyacrylamide (polyacrylamide gel electrophoresis (PAGE), including denaturing and non-denaturing PAGE). Pore size of polyacrylamide gels is controlled by modulating the concentrations of acrylamide and bis-acrylamide (which cross-links the acrylamide monomers) |
| Free-flow electrophoresis (Carrier-free electrophoresis) | No matrices are used; instead, polypeptides migrate through a solution; fast, high reproducibility, compatible with downstream detection techniques; can be run under native or denaturing conditions; only small sample volumes required (although can be used as a preparative technique) |
| Electrofocusing (Isoelectrofocusing) | Polypeptides are separated by differences in their isoelectric point (pI), usually performed in gels and based on the principle that overall charge on the polypeptide is a function of pH. An ampholyte solution is used to make immobilized pH gradient (IPG) gels. The immobilized pH gradient is obtained by the continuous change in the ratio of immobilines (weak acid or base defined by pk). Polypeptides migrate through the pH gradient until its charge is 0. Very high resolution, separating polypeptides differing by a single charge |
| Isotachophoresis (ITP) | Orders and concentrates polypeptides of intermediate effective mobilities between an ion of high effective mobility and one of much lower effective mobility, followed by their migration at a uniform speed. A multianalyte sample is introduced between the leading electrolyte (LE, containing leading ion) and the terminating electrolyte (TE, containing terminating ion) where the leading ion, the terminating ion, and the sample components have the same charge polarity, and the sample ions must have lower electrophoretic mobilities than the leading ion but larger than the terminating ion. After electrophoresis, the polypeptides move forward behind the leading ion and in front of the terminating ion, forming discrete, contiguous zones in order of their electrophoretic mobilities. Transient ITP includes an additional step of separating after ITP with zone electrophoresis. |
| Affinity electrophoresis | Based on changes in the electrophoretic pattern of molecules through specific interactions with other molecules or complex formation; examples include mobility shift, charge shift and affinity capillary electrophoresis. Various types are known, including those using agarose gel, rapid agarose gel, boronate affinity, affinity-trap polyacrylamide, and phosphate affinity electrophoresis |
| Immunoelectrophoresis | Separates polypeptides based on electrophoresis and reaction with antibodies. Includes immunoelectrophoretic analysis (one-dimensional immunoelectrophoresis), crossed immunoelectrophoresis (two-dimensional quantitative immunoelectrophoresis), rocket-immunoelectrophoresis (one-dimensional quantitative immunoelectrophoresis), fused rocket immunoelectrophoresis, and affinity immunoelectrophoresis. Often uses agarose gels buffered at high pH |
| Counterelectrophoresis (counterimmunoelectrophoresis) | Antibody and antigen migrate through a buffered diffusion medium. Antigens in a gel with a controlled pH are strongly negatively charged and migrate rapidly across the electric field toward the anode. The antibody in such a medium is less negatively charged and migrates in the opposite direction toward the cathode. If the antigen and antibody are specific for each other, they combine and form a distinct precipitin line. |

TABLE 5-continued

Examples of electrophoretic methods

| Technique | Description |
| --- | --- |
| Capillary electrophoresis | Refers to electrokinetic separation methods performed in submillimeter diameter capillaries and in micro- and nanofluidic channels. Examples include capillary zone electrophoresis (CZE), capillary gel electrophoresis (CGE), capillary isoelectric focusing (CIEF), capillary isotachophoresis and micellar electrokinetic chromatography (MEKC). |
| Capillary zone electrophoresis | A type of capillary electrophoresis, CZE separates ions based on their charge and frictional forces within a fine bore capillary. Sensitive in the picomolar range |

Prepared polypeptides can be analyzed also using spectrometric methods-mass spectrometry (Rubakhin and Sweedler, 2010), ultraviolet spectrometry, visible light spectrometry, fluorescent spectrometry, and ultraviolet-visible light spectrometry (Nowicka-Jankowska, 1986).

Table 6 presents examples of polypeptide electrophoretic techniques.

TABLE 6

Examples of Spectrometric Methods

| Technique | Description |
| --- | --- |
| Mass Spectrometry (MS) | Sample molecules are ionized by high energy electrons. The mass to charge ratio of these ions is measured by electrostatic acceleration and magnetic field perturbation, providing a precise molecular weight. Ion fragmentation patterns may be related to the structure of the molecular ion. Mass spectrum is a plot of the ion signal as a function of the mass-to-charge ratio. Analyzers include sector field mass, time-of-flight (TOF), and quadrupole mass analyzers. Ion traps include three-dimensional quadrupole, cylindrical, linear quadrupole, and Orbitrap ion traps. Detectors include electron multipliers, Faraday cups, and ion-to-photon detectors. Variations of MS include tandem MS. Mass spectrometers can be configured in a variety of ways, including matrix-assisted laser desorption/ionization source configured with a TOF analyzer (MALDI-TOF); electrospray ionization-mass spectrometry (ESI-MS), inductively coupled plasma-mass spectrometry (ICP-MS), accelerator mass spectrometry (AMS), thermal ionization-mass spectrometry (TIMS), and spark source mass spectrometry (SSMS). |
| Ultraviolet-Visible Spectroscopy | Absorption of high-energy UV light causes electronic excitation. Wavelengths of 200 to 800 nm show absorption if conjugated pi-electron systems are present |
| Infrared Spectroscopy | Absorption of infrared radiation causes vibrational and rotational excitation of groups of atoms within the polypeptide. Because of their characteristic absorptions, functional groups are identified |

The principle enabling mass spectrometry (MS) consists of ionizing chemical compounds to generate charged molecules or molecule fragments, and then measuring their mass-to-charge ratios. In an illustrative MS procedure, a sample is loaded onto the MS instrument and undergoes vaporization, the components of the sample are ionized by one of a variety of methods (e.g., by impacting them with an electron beam), which results in the formation of positively charged particles, the positive ions are then accelerated by a magnetic field, computations are performed on the mass-to-charge ratio (m/z) of the particles based on the details of motion of the ions as they transit through electromagnetic fields, and, detection of the ions, which have been sorted according to their m/z ratios.

An illustrative MS instrument has three modules: an ion source, which converts gas phase sample molecules into ions (or, in the case of electrospray ionization, move ions that exist in solution into the gas phase); a mass analyzer, which sorts the ions by their mass-to-charge ratios by applying electromagnetic fields; and a detector, which measures the value of an indicator quantity and thus provides data for calculating the abundances of each ion present.

The MS technique has both qualitative and quantitative uses, including identifying unknown compounds, determining the isotopic composition of elements in a molecule, and determining the structure of a compound by observing its fragmentation. Included are gas chromatography-mass spectrometry (GC/MS or GC-MS), liquid chromatography mass spectrometry (LC/MS or LC-MS), and ion mobility spectrometry/mass spectrometry (IMS/MS or IMMS).

The analytical methods (chromatographic, electrophoretic, and spectrometric) can be combined. For example, combinations such as liquid chromatography-mass spectrometry, capillary zone electrophoresis coupled to mass spectrometry, and ion mobility spectrometry-mass spectrometry.

Automation

The various steps of the disclosed methods can be accomplished using liquid handling robots. Such robots dispense reagents, samples or other liquids to a designated container. Robots are controlled by software, either integrated directly into the robot itself, or by a connected computer.

By automating liquid handling, the disclosed methods can be accomplished with high through-put, fewer errors, and reduced analyst hands-on time.

Liquid handling robots can be configured to use various laboratory instruments, such as centrifuges, PCR machines, colony pickers, shaking devices, heating devices, etc. Such customization permits adapting these machines to a particular method.

In some cases, such robots replace the use of pipettes and/or syringes by using sound to move liquids (acoustic liquid handling).

Currently, Agilent Technologies (Santa Clara, CA), Beckman Coulter, Inc. (Indianapolis, IN), Eppendorf North America (Hauppauge, NY), Hamilton Robotics (Reno, NV), Hudson Robotics, Inc. (Springfield, NJ), and Tecan A G (Männedorf, Switzerland) are some of the manufacturers of such robots.

Therapeutic Polypeptides

Polypeptides, including those that bind to one or more of the following, can be prepared and analyzed in the disclosed methods. These include CD proteins, including CD3, CD4, CD8, CD19, CD20, CD22, CD30, and CD34; including those that interfere with receptor binding. HER receptor family proteins, including HER2, HER3, HER4, and the EGF receptor. Cell adhesion molecules, for example, LFA-I, Mol, pl50, 95, VLA-4, ICAM-I, VCAM, and alpha v/beta 3 integrin. Growth factors, such as vascular endothelial growth factor ("VEGF"), growth hormone, thyroid stimulating hormone, follicle stimulating hormone, luteinizing hormone, growth hormone releasing factor, parathyroid hormone, Mullerian-inhibiting substance, human macrophage inflammatory protein (MIP-I-alpha), erythropoietin (EPO), nerve growth factor, such as NGF-beta, platelet-derived growth factor (PDGF), fibroblast growth factors, including, for instance, aFGF and bFGF, epidermal growth factor (EGF), transforming growth factors (TGF), including, among others, TGF-α and TGF-β, including TGF-βI, TGF-β2, TGF-β3, TGF-β4, or TGF-β5, insulin-like growth factors-I and -II (IGF-I and IGF-II), des (1-3)-IGF-I (brain IGF-I), and osteoinductive factors. Insulins and insulin-related proteins, including insulin, insulin A-chain, insulin B-chain, proinsulin, and insulin-like growth factor binding proteins. Coagulation and coagulation-related proteins, such as, among others, factor VIII, tissue factor, von Willebrands factor, protein C, alpha-1-antitrypsin, plasminogen activators, such as urokinase and tissue plasminogen activator ("t-PA"), bombazine, thrombin, and thrombopoietin; (vii) other blood and serum proteins, including but not limited to albumin, IgE, and blood group antigens. Colony stimulating factors and receptors thereof, including the following, among others, M-CSF, GM-CSF, and G-CSF, and receptors thereof, such as CSF-1 receptor (c-fms). Receptors and receptor-associated proteins, including, for example, flk2/flt3 receptor, obesity (OB) receptor, LDL receptor, growth hormone receptors, thrombopoietin receptors ("TPO-R," "c-mpl"), glucagon receptors, interleukin receptors, interferon receptors, T-cell receptors, stem cell factor receptors, such as c-Kit, and other receptors. Receptor ligands, including, for example, OX40L, the ligand for the OX40 receptor. Neurotrophic factors, including bone-derived neurotrophic factor (BDNF) and neurotrophin-3, -4, -5, or -6 (NT-3, NT-4, NT-5, or NT-6). Relaxin A-chain, relaxin B-chain, and prorelaxin; interferons and interferon receptors, including for example, interferon-α, -β, and -γ, and their receptors. Interleukins and interleukin receptors, including IL-I to IL-33 and IL-I to IL-33 receptors, such as the IL-8 receptor, among others. Viral antigens, including an AIDS envelope viral antigen. Lipoproteins, calcitonin, glucagon, atrial natriuretic factor, lung surfactant, tumor necrosis factor-alpha and -beta, enkephalinase, RANTES (regulated on activation normally T-cell expressed and secreted), mouse gonadotropin-associated peptide, DNAse, inhibin, and activin. Integrin, protein A or D, rheumatoid factors, immunotoxins, bone morphogenetic protein (BMP), superoxide dismutase, surface membrane proteins, decay accelerating factor (DAF), AIDS envelope, transport proteins, homing receptors, addressins, regulatory proteins, immunoadhesins, antibodies. Myostatins, TALL proteins, including TALL-I, amyloid proteins, including but not limited to amyloid-beta proteins, thymic stromal lymphopoietins ("TSLP"), RANK ligand ("OPGL"), c-kit, TNF receptors, including TNF Receptor Type 1, TRAIL-R2, angiopoietins, and biologically active fragments or analogs or variants of any of the foregoing.

Exemplary polypeptides and antibodies include Activase® (Alteplase); alirocumab, Aranesp® (Darbepoetin-alfa), Epogen® (Epoetin alfa, or erythropoietin); Avonex® (Interferon β-la); Bexxar® (Tositumomab); Betaseron® (Interferon-β); bococizumab (anti-PCSK9 monoclonal antibody designated as L1L3, see U.S. Pat. No. 8,080,243); Campath® (Alemtuzumab); Dynepo® (Epoetin delta); Velcade® (bortezomib); MLN0002 (anti-α4β7 mAb); MLN1202 (anti-CCR2 chemokine receptor mAb); Enbrel® (etanercept); Eprex® (Epoetin alfa); Erbitux® (Cetuximab); evolocumab; Genotropin® (Somatropin); Herceptin® (Trastuzumab); Humatrope® (somatropin [rDNA origin] for injection); Humira® (Adalimumab); Infergen® (Interferon Alfacon-1); Natrecor® (nesiritide); Kineret® (Anakinra), Leukine® (Sargamostim); LymphoCide® (Epratuzumab); Benlysta™ (Belimumab); Metalyse® (Tenecteplase); Mircera® (methoxy polyethylene glycol-epoetin beta); Mylotarg® (Gemtuzumab ozogamicin); Raptiva® (efalizumab); Cimzia® (certolizumab pegol); Soliris™ (Eculizumab); Pexelizumab (Anti-C5 Complement); MEDI-524 (Numax®); Lucentis® (Ranibizumab); Edrecolomab (Panorex®); Trabio® (lerdelimumab); TheraCim hR3 (Nimotuzumab); Omnitarg (Pertuzumab, 2C4); Osidem® (IDM-I); OvaRex® (B43.13); Nuvion® (visilizumab); Cantuzumab mertansine (huC242-DMI); NeoRecormon® (Epoetin beta); Neumega® (Oprelvekin); Neulasta® (Pegylated filgastrim, pegylated G-CSF, pegylated hu-Met-G-CSF); Neupogen® (Filgrastim); Orthoclone OKT3® (Muromonab-CD3), Procrit® (Epoetin alfa); Remicade® (Infliximab), Reopro® (Abciximab), Actemra® (anti-IL6 Receptor mAb), Avastin® (Bevacizumab), HuMax-CD4 (zanolimumab), Rituxan® (Rituximab); Tarceva® (Erlotinib); Roferon-A®-(Interferon alfa-2a); Simulect® (Basiliximab); Stelara™ (Ustekinumab); Prexige® (lumiracoxib); Synagis® (Palivizumab); 146B7-CHO (anti-IL15 antibody, see U.S. Pat. No. 7,153,507), Tysabri® (Natalizumab); Valortim® (MDX-1303, anti-B. anthracis Protective Antigen mAb); ABthrax™; Vectibix® (Panitumumab); Xolair® (Omalizumab), ETI211 (anti-MRSA mAb), IL-I Trap (the Fc portion of human IgGI and the extracellular domains of both IL-I receptor components (the Type I receptor and receptor accessory protein)), VEGF Trap (lg domains of VEGFR1 fused to IgGI Fc), Zenapax® (Daclizumab); Zenapax® (Daclizumab), Zevalin® (Ibritumomab tiuxetan), Zetia (ezetimibe), Atacicept (TACI-Ig), anti-α4β7 mAb (vedolizumab); galiximab (anti-CD80 monoclonal antibody), anti- CD23 mAb (lumiliximab); BR2-Fc (huBR3/huFc fusion protein, soluble BAFF antagonist); Simponi™ (Golimumab); Mapatumumab (human anti-TRAIL Receptor-1 mAb); Ocrelizumab (anti-CD20 human mAb); HuMax-EGFR (zalutumumab); M200 (Volociximab, anti-α5β1 integrin mAb); MDX-010 (Ipilimumab, anti-CTLA-4 mAb and VEGFR-I (IMC-18F1); anti-BR3 mAb; anti-*C. difficile* Toxin A and Toxin B C mAbs MDX-066 (CDA-I) and MDX-1388); anti-CD22 dsFv-PE38 conjugates (CAT-3888 and CAT-8015); anti-CD25 mAb (HuMax-TAC); anti-TSLP antibodies; anti-TSLP receptor antibody (U.S. Pat. No. 8,101,182); anti-TSLP antibody designated as A5 (U.S. Pat. No. 7,982,016); (anti-CD3 mAb (NI-0401); Adecatumumab (MT201, anti-EpCAM-CD326 mAb); MDX-060, SGN-30, SGN-35 (anti-CD30 mAbs); MDX-1333 (anti-IFNAR); HuMax CD38 (anti-CD38 mAb); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-sclerostin antibodies (see, U.S. Pat. No. 8,715,663 or U.S. Pat. No. 7,592,429) anti-sclerostin antibody designated as Ab-5 (U.S. Pat. No. 8,715,663 or U.S. Pat. No. 7,592,429); anti-ganglioside GM2 mAb; anti-GDF-8 human mAb (MYO-029); anti-GM-CSF Receptor mAb (CAM-3001); anti-HepC mAb (HuMax HepC); MEDI-545, MDX-1103 (anti-IFNα mAb); anti-IGFIR mAb; anti-IGF-IR mAb (HuMax-Inflam); anti-IL12/IL23p40 mAb (Briakinumab); anti-IL-23p19 mAb (LY2525623); anti-IL13 mAb (CAT-354); anti-IL-17 mAb (AIN457); anti-IL2Ra mAb (HuMax-TAC); anti-IL5 Receptor mAb; anti-integrin receptors mAb (MDX-O18, CNTO 95); anti-IPIO Ulcerative Colitis mAb (MDX-1100); anti-LLY antibody; BMS-66513; anti-Mannose Receptor/hCGB mAb (MDX-1307); anti-mesothelin dsFv-PE38 conjugate (CAT-5001); anti-PDImAb (MDX-1 106 (ONO-4538)); anti-PDGFRa antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; NVS Antibody #2; and an amyloid-beta monoclonal antibody comprising sequences, SEQ ID NO:8 and SEQ ID NO:6 (U.S. Pat. No. 7,906,625).

Examples of antibodies suitable for the methods and pharmaceutical formulations include the antibodies shown in Table 1. Other examples of suitable antibodies include infliximab, bevacizumab, cetuximab, ranibizumab, palivizumab, abagovomab, abciximab, actoxumab, adalimumab, afelimomab, afutuzumab, alacizumab, alacizumab pegol, ald518, alemtuzumab, alirocumab, altumomab, amatuximab, anatumomab mafenatox, anrukinzumab, apolizumab, arcitumomab, aselizumab, altinumab, atlizumab, atorolimiumab, tocilizumab, bapineuzumab, basiliximab, bavituximab, bectumomab, belimumab, benralizumab, bertilimumab, besilesomab, bevacizumab, bezlotoxumab, biciromab, bivatuzumab, bivatuzumab mertansine, blinatumomab, blosozumab, brentuximab vedotin, briakinumab, brodalumab, canakinumab, cantuzumab mertansine, cantuzumab mertansine, caplacizumab, capromab pendetide, carlumab, catumaxomab, cc49, cedelizumab, certolizumab pegol, cetuximab, citatuzumab bogatox, cixutumumab, clazakizumab, clenoliximab, clivatuzumab tetraxetan, conatumumab, crenezumab, cr6261, dacetuzumab, daclizumab, dalotuzumab, daratumumab, demcizumab, denosumab, detumomab, dorlimomab aritox, drozitumab, duligotumab, dupilumab, ecromeximab, eculizumab, edobacomab, edrecolomab, efalizumab, efungumab, elotuzumab, elsilimomab, enavatuzumab, enlimomab pegol, enokizumab, enoticumab, ensituximab, epitumomab cituxetan, epratuzumab, erenumab, erlizumab, ertumaxomab, etaracizumab, etrolizumab, evolocumab, exbivirumab, fanolesomab, faralimomab, farletuzumab, fasinumab, fbta05, felvizumab, fezakinumab, ficlatuzumab, figitumumab, flanvotumab, fontolizumab, foralumab, foravirumab, fresolimumab, fulranumab, futuximab, galiximab, ganitumab, gantenerumab, gavilimomab, gemtuzumab ozogamicin, gevokizumab, girentuximab, glembatumumab vedotin, golimumab, gomiliximab, gs6624, ibalizumab, ibritumomab tiuxetan, icrucumab, igovomab, imciromab, imgatuzumab, inclacumab, indatuximab ravtansine, infliximab, intetumumab, inolimomab, inotuzumab ozogamicin, ipilimumab, iratumumab, itolizumab, ixekizumab, keliximab, labetuzumab, lebrikizumab, lemalesomab, lerdelimumab, lexatumumab, libivirumab, ligelizumab, lintuzumab, lirilumab, lorvotuzumab mertansine, lucatumumab, lumiliximab, mapatumumab, maslimomab, mavrilimumab, matuzumab, mepolizumab, metelimumab, milatuzumab, minretumomab, mitumomab, mogamulizumab, morolimumab, motavizumab, moxetumomab pasudotox, muromonab-cd3, nacolomab tafenatox, namilumab, naptumomab estafenatox, narnatumab, natalizumab, nebacumab, necitumumab, nerelimomab, nesvacumab, nimotuzumab, nivolumab, nofetumomab merpentan, ocaratuzumab, ocrelizumab, odulimomab, ofatumumab, olaratumab, olokizumab, omalizumab, onartuzumab, oportuzumab monatox, oregovomab, orticumab, otelixizumab, oxelumab, ozanezumab, ozoralizumab, pagibaximab, palivizumab, panitumumab, panobacumab, parsatuzumab, pascolizumab, pateclizumab, patritumab, pemtumomab, perakizumab, pertuzumab, pexelizumab, pidilizumab, pintumomab, placulumab, ponezumab, priliximab, pritumumab, PRO 140, quilizumab, racotumomab, radretumab, rafivirumab, ramucirumab, ranibizumab, raxibacumab, regavirumab, reslizumab, rilotumumab, rituximab, robatumumab, roledumab, romosozumab, rontalizumab, rovelizumab, ruplizumab, samalizumab, sarilumab, satumomab pendetide, secukinumab, sevirumab, sibrotuzumab, sifalimumab, siltuximab, simtuzumab, siplizumab, sirukumab, solanezumab, solitomab, sonepcizumab, sontuzumab, stamulumab, sulesomab, suvizumab, tabalumab, tacatuzumab tetraxetan, tadocizumab, talizumab, tanezumab, taplitumomab paptox, tefibazumab, telimomab aritox, tenatumomab, tefibazumab, teneliximab, teplizumab, teprotumumab, TGN1412, tremelimumab, ticilimumab, tildrakizumab, tigatuzumab, TNX-650, tocilizumab, toralizumab, tositumomab, tralokinumab, trastuzumab, TRBS07, tregalizumab, tucotuzumab celmoleukin, tuvirumab, ublituximab, urelumab, urtoxazumab, ustekinumab, vapaliximab, vatelizumab, vedolizumab, veltuzumab, vepalimomab, vesencumab, visilizumab, volociximab, vorsetuzumab mafodotin, votumumab, zalutumumab, zanolimumab, zatuximab, ziralimumab, zolimomab aritox.

Antibodies also include adalimumab, bevacizumab, blinatumomab, cetuximab, conatumumab, denosumab, eculizumab, erenumab, evolocumab, infliximab, natalizumab, panitumumab, rilotumumab, rituximab, romosozumab, tezepelumab, and trastuzumab, and antibodies selected from Table 7.

TABLE 7

| Target (informal name) | HC Type (including allotypes) | LC Type | pI | LC SEQ ID NO | HC SEQ ID NO |
|---|---|---|---|---|---|
| anti-amyloid | IgG1 (f) (R; EM) | Kappa | 9.0 | 18 | 19 |
| GMCSF (247) | IgG2 | Kappa | 8.7 | 20 | 21 |
| CGRPR | IgG2 | Lambda | 8.6 | 22 | 23 |
| RANKL | IgG2 | Kappa | 8.6 | 24 | 25 |
| Sclerostin (27H6) | IgG2 | Kappa | 6.6 | 26 | 27 |
| IL-1R1 | IgG2 | Kappa | 7.4 | 28 | 29 |
| Myostatin | IgG1 (z) (K; EM) | Kappa | 8.7 | 30 | 31 |
| B7RP1 | IgG2 | Kappa | 7.7 | 32 | 33 |
| Amyloid | IgG1 (za) (K; DL) | Kappa | 8.7 | 34 | 35 |
| GMCSF (3.112) | IgG2 | Kappa | 8.8 | 36 | 37 |
| CGRP (32H7) | IgG2 | Kappa | 8.7 | 38 | 39 |
| CGRP (3B6.2) | IgG2 | Lambda | 8.6 | 40 | 41 |
| PCSK9 (8A3.1) | IgG2 | Kappa | 6.7 | 42 | 43 |
| PCSK9 (492) | IgG2 | Kappa | 6.9 | 44 | 45 |
| CGRP | IgG2 | Lambda | 8.8 | 46 | 47 |
| Hepcidin | IgG2 | Lambda | 7.3 | 48 | 49 |
| TNFR p55 ) | IgG2 | Kappa | 8.2 | 50 | 51 |
| OX40L | IgG2 | Kappa | 8.7 | 52 | 53 |
| HGF | IgG2 | Kappa | 8.1 | 54 | 55 |
| GMCSF | IgG2 | Kappa | 8.1 | 56 | 57 |
| Glucagon R | IgG2 | Kappa | 8.4 | 58 | 59 |
| GMCSF (4.381) | IgG2 | Kappa | 8.4 | 60 | 61 |
| Sclerostin (13F3) | IgG2 | Kappa | 7.8 | 62 | 63 |
| CD-22 | IgG1 (f) (R; EM) | Kappa | 8.8 | 64 | 65 |
| INFgR | IgG1 (za) (K; DL) | Kappa | 8.8 | 66 | 67 |
| Ang2 | IgG2 | Kappa | 7.4 | 68 | 69 |
| TRAILR2 | IgG1 (f) (R; EM) | Kappa | 8.7 | 70 | 71 |
| EGFR | IgG2 | Kappa | 6.8 | 72 | 73 |
| IL-4R | IgG2 | Kappa | 8.6 | 74 | 75 |
| IL-15 | IgG1 (f) (R; EM) | Kappa | 8.8 | 76 | 77 |
| IGF1R | IgG1 (za) (K; DL) | Kappa | 8.6 | 78 | 79 |
| IL-17R | IgG2 | Kappa | 8.6 | 80 | 81 |
| Dkk1 (6.37.5) | IgG2 | Kappa | 8.2 | 82 | 83 |
| Sclerostin | IgG2 | Kappa | 7.4 | 84 | 85 |
| TSLP | IgG2 | Lambda | 7.2 | 86 | 87 |
| Dkk1 (11H10) | IgG2 | Kappa | 8.2 | 88 | 89 |
| PCSK9 | IgG2 | Lambda | 8.1 | 90 | 91 |
| GIPR (2G10.006) | IgG1 (z) (K; EM) | Kappa | 8.1 | 92 | 93 |
| Activin | IgG2 | Lambda | 7.0 | 94 | 95 |
| Sclerostin (2B8) | IgG2 | Lambda | 6.7 | 96 | 97 |
| Sclerostin | IgG2 | Kappa | 6.8 | 98 | 99 |
| c-fms | IgG2 | Kappa | 6.6 | 100 | 101 |
| α4β7 | IgG2 | Kappa | 6.5 | 102 | 103 |

*HC-antibody heavy chain; LC-antibody light chain.

In some embodiments, the therapeutic polypeptide is a BiTE®. BiTE®s are engineered bispecific monoclonal antibodies which direct the cytotoxic activity of T cells against cancer cells. One of the scFvs binds to T cells via the CD3 receptor, and the other to a tumor cell via a tumor specific molecule. Blinatumomab (BLINCYTO®) is an example of a BiTE®, specific for CD19.

EXAMPLES

The following Examples section is given solely by way of example and are not set forth to limit the disclosure or claims in any way.

Example 1—Filter Equilibration and Concentration

Add 200 μL of Denaturing Solution (6 M Guanidine HCl, 200 mM Tris-HCl, 20 mM Methionine, pH 8.3 (100 mL)) to the filter unit and centrifuge at 14000×g for 10 mins. Discard the flow-through.

Add 100 μg of BITER-1 to a Microcon 30K filter unit and centrifuge at 14,000×g for 10 mins. Discard the flow-through.

Reduction and Alkylation

For each sample, add 3 μL 0.5 M DTT to 37 μL Denaturing Solution. Add 40 μL of this solution to each filter and incubate at 37° C. for 30 min.

For each sample, add 7 μL 0.5 M Sodium Iodoacetate to 33 μL Denaturing Solution. Add 40 μL of this solution to each filter and incubate at 25° C. in dark for 20 min.

For each sample, add 4 μL 0.5 M DTT to 36 μL Denaturing Solution. Add 40 μL of this solution to each filter to quench alkylation.

Centrifuge the filter at 14,000×g for 15 mins. Discard the flow-through.

Example 2—Tryptic Digestion

Add 200 μL Digestion Solution (50 mM Tris-HCl, 20 mM Methionine, pH 7.8 (100 mL)) to the filter unit and centrifuge at 14,000×g for 15 mins. Discard the flow-through. Repeat this step two more times.

Add 5 μL Trypsin Solution (1 mg/ml Trypsin) to 35 μl Digestion Solution. Add 40 μL of this solution to each filter (enzyme to protein ratio 1:20). Gently mix for 1 min on the vortex. Incubate at 37° C. for 1 hour.

Transfer the filter to a new collection tube (tube 2) and centrifuge at 14,000×g for 10 mins. Retain the flow-through in tube 2. Tube 2 will now contain the trypic fragments below 30 kDa. Retain the original collection tube (tube 1) for subsequent digestions and filtrations.

Add 20 μL Digestion Solution to the filter and centrifuge at 14,000×g for 10 min into tube 2 to wash the membrane. Repeat this step one more time.

Transfer filter back to previously used collection tube (tube 1). Store collection tube (tube 2) used to collect tryptic peptides in previous step at 2-8° C. for up to 3 hours.

Example 3—Human Neutrophil Elastase Digest

For each sample, add 5 μL human neutrophil elastase (1 mg/ml Human Neutrophil Elastase) to 35 μl Digestion Solution. Add 40 μL of this solution to each filter (enzyme to protein ratio 1:20). Gently mix for 1 min on the vortex. Incubate at 37° C. for 30 min.

Transfer the filter to the collection tube containing tryptic peptides (tube 2) and centrifuge at 14,000×g for 10 mins. Collect the flow-through. Add 20 μL Digestion Solution to the filter and centrifuge at 14,000×g to wash the membrane. Centrifuge for 10 min into the same collection tube (tube 2).

Add 160 μL Digest Quenching Solution (8 M Guanidine-HCl, 250 mM Acetate, pH 4.7 (100 mL)) to the flow through.

Mix gently and transfer digest into appropriate HPLC vial.

Digest can be frozen at −70° C. for up to 2 weeks.

Example 4—Ultra-Performance Liquid Chromatography (UPLC) Conditions

For all samples, Mobile Phase A consisted of 0.1% formic acid in water, and Mobile Phase B consisted of 0.1% formic acid in acetonitrile. Separation was performed using either a CSH C18 1.7 μm, 2.1×150 mm UPLC column (Waters, Milford, MA, P/N 186005298) or a BEH C18 1.7 μm, 2.1×150 mm UPLC column (Waters, Milford, MA, P/N 186003556). UPLC separations were performed using either a Thermo Scientific U-3000 system (Waltham, MA), a Waters Acquity H-Class system (Milford, MA), or and Agilent 1290 system (Santa Clara, CA). Based on starting material, ~3-4 μg of sample was loaded on column.

Example 5—Mass Spectrometry Conditions

Peptides resulting from digestion were analyzed using a Thermo Scientific Q Exactive (Waltham, MA), a Thermo Scientific Q Exactive Plus (Waltham, MA), or a Thermo Scientific Q Exactive BioPharma (Waltham, MA). Because multiple instruments were used, data collection parameters varied slightly depending on the instrument. Instruments were operated in data-dependent mode (top 4-8) over a scan range of 200-2,000 m/z. The AGC target was set to 1E6 for MS1 scans and 5E5 for MSMS scans. MS1 scans were collected at a resolution of either 35,000 or 140,000, and MS2 scans were collected at a resolution of 17,500. An isolation window of 2-4 m/z was specified for MSMS scans. Peaks with unassigned charge states and charge states greater than 8 were excluded from MSMS. Dynamic exclusion was set to 10 s. Lock Mass of m/z 391.28430 was enabled.

Example 6—Data Analysis

MS data were searched with MassAnalyzer. Carboxymethylation was specified as a static modification. For all searches, signal-to-noise ratio was set to 20, mass accuracy of 15 ppm was specified, and confidence was set to 0.95. For sequence coverage maps, minimum peak area was set to 1% of the base peak, relative peak area threshold was set to 17%, minimum confidence was set to 0.95, and maximum peptide mass was set to 15,000.

REFERENCES

All references are incorporated herein by reference in their entireties.

Crimmins, D. L., S. M. Mische, and N. D. Denslow. 2001. Chemical Cleavage of Proteins in Solution. In Current Protocols in Protein Science. John Wiley & Sons, Inc.

Doucet, A., and C. M. Overall. 2011. Broad coverage identification of multiple proteolytic cleavage site sequences in complex high molecular weight proteins using quantitative proteomics as a complement to edman sequencing. *Molecular & cellular proteomics: MCP.* 10: M110 003533.

Gunzler, H., and A. Williams. 2001. Handbook of analytical techniques. Wiley-VCH, Weinheim, Germany. 1198 pp.

Janoff, A., and J. Scherer. 1968. Mediators of inflammation in leukocyte lysosomes. IX. Elastinolytic activity in granules of human polymorphonuclear leukocytes. *J Exp Med.* 128:1137-1155.

Kurien, B. T., and R. H. Scofield. 2012. Protein electrophoresis: methods and protocols. Humana Press; Springer, New York. xiv, 648 p. pp.

Li, A., R. C. Sowder, L. E. Henderson, S. P. Moore, D. J. Garfinkel, and R. J. Fisher. 2001. Chemical Cleavage at Aspartyl Residues for Protein Identification. *Analytical Chemistry.* 73:5395-5402.

Lord, G. A. 2004. Capillary electrophoresis of proteins and peptides, Edited by M. A. Strege and A. L. Lagu (Methods in Molecular Biology, Volume 276, Series Editor J. M. Walker). Humana Press, Totowa, New Jersey, 2004, 332 pp, US$125.00. *Biomedical Chromatography.* 18:875-875.

Nowicka-Jankowska, T. 1986. Analytical visible and ultraviolet spectrometry. Elsevier; Distributors for the United States and Canada, Elsevier Science Pub. Co., Amsterdam; New York New York, NY, USA. xvi, 690 p. pp.

Pontius, J., L. Wagner, and G. Schuler. 2003. UniGene: a unified view of teh transcriptome. In The NCBI Handbook. National Center for Biotechnology Information, Bethesda (MD).

Rawlings, N. D., M. Waller, A. J. Barrett, and A. Bateman. 2014. MEROPS: the database of proteolytic enzymes, their substrates and inhibitors. *Nucleic acids research.* 42: D503-509.

Rohani, R., M. Hyland, and D. Patterson. 2011. A refined one-filtration method for aqueous based nanofiltration and ultrafiltration membrane molecular weight cut-off determination using polyethylene glycols. *Journal of Membrane Science.* 382:278-290.

Rubakhin, S. S., and J. V. Sweedler. 2010. Mass spectrometry imaging: principles and protocols. Humana Press, New York. xiv, 487 p. pp.

Sinha, S., W. Watorek, S. Karr, J. Giles, W. Bode, and J. Travis. 1987. Primary structure of human neutrophil elastase. *Proc Natl Acad Sci USA.* 84:2228-2232.

Stein, R. L., A. M. Strimpler, H. Hori, and J. C. Powers. 1987. Catalysis by human leukocyte elastase: mechanistic insights into specificity requirements. *Biochemistry.* 26:1301-1305.

Tanabe, K., A. Taniguchi, T. Matsumoto, K. Oisaki, Y. Sohma, and M. Kanai. 2014. Asparagine-selective cleavage of peptide bonds through hypervalent iodine-mediated Hofmann rearrangement in neutral aqueous solution. *Chemical Science*. 5:2747-2753.

Tanford, C. 1968. Protein Denaturation. In Advances in Protein Chemistry. Vol. 23. C. B. Anfinsen, M. L. Anson, J. T. Edsall, and F. M. Richards, editors. Academic Press. 121-282.

The UniProt, C. 2017. UniProt: the universal protein knowledgebase. *Nucleic acids research*. 45: D158-D169.

Unspecified. 2007. Table 2. List of proteases commonly used for fragmenting proteins. *Cold Spring Harbor Protocols*. 2007: pdb.tab2ip13.

Wisniewski, J. R., A. Zougman, N. Nagaraj, and M. Mann. 2009. Universal sample preparation method for proteome analysis. *Nature methods*. 6:359-362.

The invention claimed is:

1. A method of preparing a therapeutic polypeptide for analysis, comprising:
   a. cleaving the polypeptide in a first digestion, wherein the cleaving produces at least two fragments of the polypeptide;
   b. separating the at least two fragments from each other to produce a first large peptide fragment-containing solution and a first small peptide fragment-containing solution;
   c. cleaving the large peptide fragments of the first large peptide fragment-containing solution in a second digestion, wherein at least one of the large peptide fragments of the first large peptide fragment-containing solution is cleaved to produce at least two fragments of the large peptide fragments of the first large peptide fragment-containing solution;
   d. combining the digested solution of c. and the small peptide fragment-containing solution of b; and
   e. analyzing the combined solution of d.

2. The method of claim 1, wherein the cleaving the polypeptide in the first digestion comprises proteolytic or chemical cleavage.

3. The method of claim 2, wherein the cleaving is proteolytic cleavage accomplished by a protease.

4. The method of claim 3, wherein the protease is selected from the group consisting of neutrophil elastase, trypsin, endoproteinase Glu-C, endoproteinase Arg-C, pepsin, chymotrypsin, chymotrypsin B, Lys-N protease, Lys-C protease, Glu-C protease, Asp-N protease, pancreatopeptidase, carboxypeptidase A, carboxypeptidase B, proteinase K, and thermolysin, and combinations thereof.

5. The method of claim 4, wherein the protease is trypsin.

6. The method of claim 1, wherein the polypeptide is denatured before cleaving the polypeptide in the sample in the first digestion.

7. The method of claim 1, wherein the polypeptide is alkylated before cleaving the polypeptide in the sample in the first digestion.

8. The method of claim 1, wherein the polypeptide is denatured and either alkylated or reduced before cleaving the polypeptide in the sample in the first digestion.

9. The method of claim 1, wherein the polypeptide is denatured, reduced, and alkylated before cleaving the polypeptide in the sample in the first digestion.

10. The method of claim 1, wherein the cleaving the polypeptide in the second digestion comprises proteolytic cleavage accomplished by a protease.

11. The method of claim 10, wherein the protease is selected from the group consisting of neutrophil elastase, trypsin, endoproteinase Glu-C, endoproteinase Arg-C, pepsin, chymotrypsin, chymotrypsin B, Lys-N protease, Lys-C protease, Glu-C protease, Asp-N protease, pancreatopeptidase, carboxypeptidase A, carboxypeptidase B, proteinase K, and thermolysin, and combinations thereof; wherein the protease is different than the protease used for cleaving the polypeptide in the first digestion.

12. The method of claim 11, wherein the protease is neutrophil elastase.

13. The method of claim 12, wherein the neutrophil elastase is human neutrophil elastase.

14. The method of claim 1, wherein analyzing comprises at least one technique selected from the group consisting of chromatography, electrophoresis, spectrometry, and combinations thereof.

15. The method of claim 14, wherein the technique for analyzing the sample comprises:
   a. chromatography and is selected from the group consisting of gas chromatography, liquid chromatography, high performance liquid chromatography, ultra-performance liquid chromatography, size-exclusion chromatography, ion-exchange chromatography, affinity chromatography, expanded bed adsorption chromatography, reverse-phase chromatography, hydrophobic interaction chromatography, and combinations thereof;
   b. electrophoresis and is selected from the group consisting of gel electrophoresis, free-flow electrophoresis, electrofocusing, isotachophoresis, affinity electrophoresis, immunoelectrophoresis, counterelectrophoresis, and capillary electrophoresis, capillary zone electrophoresis, and combinations thereof; or
   c. spectrometry and is selected from the group consisting of mass spectrometry, ultraviolet spectrometry, visible light spectrometry, fluorescent spectrometry, and ultraviolet-visible light spectrometry, and combinations thereof.

16. The method of claim 15, wherein the technique comprises liquid chromatography-mass spectrometry.

17. The method of claim 1, wherein the at least two fragments of step a. are separated using a molecular weight cutoff filter.

18. The method of claim 17, wherein the molecular cutoff of the filter is 30 kDa.

19. The method of claim 1, wherein the method is at least partially executed by an automated liquid handling device.

20. The method of claim 1, wherein the therapeutic polypeptide is selected from the group consisting of an antibody or antigen-binding fragment thereof, a derivative of an antibody or antibody fragment, and a fusion polypeptide.

21. The method of claim 20, wherein the therapeutic polypeptide is selected from the group consisting of infliximab, bevacizumab, cetuximab, ranibizumab, palivizumab, abagovomab, abciximab, actoxumab, adalimumab, afelimomab, afutuzumab, alacizumab, alacizumab pegol, ald518, alemtuzumab, alirocumab, altumomab, amatuximab, anatumomab mafenatox, anrukinzumab, apolizumab, arcitumomab, aselizumab, altinumab, atlizumab, atorolimiumab, tocilizumab, bapineuzumab, basiliximab, bavituximab, bectumomab, belimumab, benralizumab, bertilimumab, besilesomab, bevacizumab, bezlotoxumab, biciromab, bivatuzumab, bivatuzumab mertansine, blinatumomab, blosozumab, brentuximab vedotin, briakinumab, brodalumab, canakinumab, cantuzumab mertansine, cantuzumab mertansine, caplacizumab, capromab pendetide, carlumab, catumaxomab, cc49, cedelizumab, certolizumab pegol, cetuximab, citatuzumab bogatox, cixutumumab, clazakizumab, clenoliximab, clivatuzumab tetraxetan, conatumumab, crenezumab, cr6261, dacetuzumab, daclizumab, dalotuzumab, daratumumab, demcizumab, denosumab, detumomab, dorlimomab aritox, drozitumab, duligotumab, dupilumab, ecromeximab, eculizumab, edobacomab, edrecolomab, efalizumab, efungumab, elotuzumab, elsilimomab, enavatuzumab, enlimomab pegol, enokizumab, enoticumab, ensituximab, epitumomab cituxetan, epratuzumab, erenumab, erlizumab, ertumaxomab, etaracizumab, etrolizumab, evolocumab, exbivirumab, fanolesomab, faralimomab, farletuzumab, fasinumab, fbta05, felvizumab, fezakinumab, ficlatuzumab, figitumumab, flanvotumab, fontolizumab, foralumab, foravirumab, fresolimumab, fulranumab, futuximab, galiximab, ganitumab, gantenerumab, gavilimomab, gemtuzumab ozogamicin, gevokizumab, girentuximab, glembatumumab vedotin, golimumab, gomiliximab, gs6624, ibalizumab, ibritumomab tiuxetan, icrucumab, igovomab, imciromab, imgatuzumab, inclacumab, indatuximab ravtansine, infliximab, intetumumab, inolimomab, inotuzumab ozogamicin, ipilimumab, iratumumab, itolizumab, ixekizumab, keliximab, labetuzumab, lebrikizumab, lemalesomab, lerdelimumab, lexatumumab, libivirumab, ligelizumab, lintuzumab, lirilumab, lorvotuzumab mertansine, lucatumumab, lumiliximab, mapatumumab, maslimomab, mavrilimumab, matuzumab, mepolizumab, metelimumab, milatuzumab, minretumomab, mitumomab, mogamulizumab, morolimumab, motavizumab, moxetumomab pasudotox, muromonab-cd3, nacolomab tafenatox, namilumab, naptumomab estafenatox, narnatumab, natalizumab, nebacumab, necitumumab, nerelimomab, nesvacumab, nimotuzumab, nivolumab, nofetumomab merpentan, ocaratuzumab, ocrelizumab, odulimomab, ofatumumab, olaratumab, olokizumab, omalizumab, onartuzumab, oportuzumab monatox, oregovomab, orticumab, otelixizumab, oxelumab, ozanezumab, ozoralizumab, pagibaximab, palivizumab, panitumumab, panobacumab, parsatuzumab, pascolizumab, pateclizumab, patritumab, pemtumomab, perakizumab, pertuzumab, pexelizumab, pidilizumab, pintumomab, placulumab, ponezumab, priliximab, pritumumab, PRO 140, quilizumab, racotumomab, radretumab, rafivirumab, ramucirumab, ranibizumab, raxibacumab, regavirumab, reslizumab, rilotumumab, rituximab, robatumumab, roledumab, romosozumab, rontalizumab, rovelizumab, ruplizumab, samalizumab, sarilumab, satumomab pendetide, secukinumab, sevirumab, sibrotuzumab, sifalimumab, siltuximab, simtuzumab, siplizumab, sirukumab, solanezumab, solitomab, sonepcizumab, sontuzumab, stamulumab, sulesomab, suvizumab, tabalumab, tacatuzumab tetraxetan, tadocizumab, talizumab, tanezumab, taplitumomab paptox, tefibazumab, telimomab aritox, tenatumomab, tefibazumab, teneliximab, teplizumab, teprotumumab, tezepelumab, TGN1412, tremelimumab, ticilimumab, tildrakizumab, tigatuzumab, TNX-650, tocilizumab, toralizumab, tositumomab, tralokinumab, trastuzumab, TRBS07, tregalizumab, tucotuzumab celmoleukin, tuvirumab, ubliuximab, urelumab, urtoxazumab, ustekinumab, vapaliximab, vatelizumab, vedolizumab, veltuzumab, vepalimomab, vesencumab, visilizumab, volociximab, vorsetuzumab mafodotin, votumumab, zalutumumab, zanolimumab, zatuximab, ziralimumab, zolimomab aritox, a glycoprotein, CD polypeptide, a HER receptor polypeptide, a cell adhesion polypeptide, a growth factor polypeptide, an insulin polypeptide, an insulin-related polypeptide, a coagulation polypeptide, a coagulation-related polypeptide, albumin, IgE, a blood group antigen, a colony stimulating factor, a receptor, a neurotrophic factor, an interferon, an interleukin, a viral antigen, a lipoprotein, calcitonin, glucagon, atrial natriuretic factor, lung surfactant, tumor necrosis factor-alpha and -beta, enkephalinase, mouse gonadotropin-associated peptide, DNAse, inhibin, activing, an integrin, protein A, protein D, a rheumatoid factor, an immunotoxin, a bone morphogenetic protein, a superoxide dismutase, a surface membrane polypeptide, a decay accelerating factor, an AIDS envelope, a transport polypeptide, a homing receptor, an addressin, a regulatory polypeptide, an immunoadhesin, a myostatin, a TALL polypeptide, an amyloid polypeptide, a thymic stromal lymphopoietin, a RANK ligand, a c-kit polypeptide, a TNF receptor, and an angiopoietin, the antibodies shown in Table 7 and biologically active fragments, analogs or variants thereof.

22. The method of claim 20, wherein the therapeutic polypeptide is a bi-specific T-cell engager molecule.

23. A method of preparing a therapeutic polypeptide for analysis, comprising:
   a. cleaving the polypeptide in a first digestion, wherein the cleaving produces at least two fragments of the polypeptide;
   b. separating the at least two fragments from each other to produce a first large peptide fragment-containing solution and a first small peptide fragment-containing solution;
   c. cleaving the large peptide fragments of the first large peptide fragment-containing solution in a second digestion, wherein at least one of the large peptide fragments of the first large peptide fragment-containing solution is cleaved to produce at least two fragments of the large peptide fragments of the first large peptide fragment-containing solution;
   d. separating the at least two fragments of the large peptide fragments from each other to produce a second large peptide fragment-containing solution and a second small peptide fragment-containing solution;
   e. cleaving the large peptide fragments of the second large peptide fragment-containing solution in a third digestion, wherein at least one of the large peptide fragments of the second large peptide fragment-containing solution is cleaved to produce at least two fragments of the large peptide fragments of the second large peptide fragment-containing solution;
   f. combining the digested solution of c., the first small peptide fragment-containing solution of b., and the second small peptide fragment-containing solution of d; and
   g. analyzing the combined solution of f.

24. The method of claim 23, wherein the cleaving the polypeptide in the third digestion comprises proteolytic cleavage accomplished by a protease.

25. The method of claim 24, wherein the protease is selected from the group consisting of neutrophil elastase, trypsin, endoproteinase Glu-C, endoproteinase Arg-C, pepsin, chymotrypsin, chymotrypsin B, Lys-N protease, Lys-C protease, Glu-C protease, Asp-N protease, pancreatopeptidase, carboxypeptidase A, carboxypeptidase B, proteinase K, and thermolysin, and combinations thereof; wherein the protease is different than the protease used for cleaving the polypeptide in the first digestion and different than the protease used for cleaving the polypeptide in the second digestion.

26. A method of preparing a therapeutic polypeptide for analysis, comprising:
   a. denaturing, reducing, and alkylating the polypeptide;
   b. digesting the polypeptide with trypsin to produce large trypsin-cleaved polypeptide fragments and small trypsin-cleaved polypeptide fragments;

c. separating the large and small trypsin-cleaved polypeptide fragments into a first aliquot and a second aliquot, respectively;
d. digesting the large trypsin-cleaved polypeptide fragments of the first aliquot with neutrophil elastase;
e. combining the first aliquot and second aliquot at about a 1:1 ratio; and
f. analyzing the combined aliquots of step (e).

27. The method of claim 26, wherein the neutrophil elastase is human neutrophil elastase.

28. The method of claim 26, wherein analyzing the sample comprises at least one technique selected from the group consisting of chromatography, electrophoresis, spectrometry, and combinations thereof.

29. The method of claim 28, wherein:
a. the technique comprises chromatography and is selected from the group consisting of gas chromatography, liquid chromatography, high performance liquid chromatography, ultra-performance liquid chromatography, size-exclusion chromatography, ion-exchange chromatography, affinity chromatography, expanded bed adsorption chromatography, reverse-phase chromatography, hydrophobic interaction chromatography, and combinations thereof;
b. the technique comprises electrophoresis and is selected from the group consisting of gel electrophoresis, free-flow electrophoresis, electrofocusing, isotachophoresis, affinity electrophoresis, immunoelectrophoresis, counterelectrophoresis, and capillary electrophoresis, and combinations thereof; or
c. the technique comprises spectrometry and is selected from the group consisting of mass spectrometry, ultraviolet spectrometry, visible light spectrometry, fluorescent spectrometry, and ultraviolet-visible light spectrometry, and combinations thereof.

30. The method of claim 26, wherein the therapeutic polypeptide is selected from the group consisting of an antibody or antigen-binding fragment thereof, a derivative of an antibody or antibody fragment, and a fusion polypeptide.

31. The method of claim 30, wherein the therapeutic polypeptide is selected from the group consisting of infliximab, bevacizumab, cetuximab, ranibizumab, palivizumab, abagovomab, abciximab, actoxumab, adalimumab, afelimomab, afutuzumab, alacizumab, alacizumab pegol, ald518, alemtuzumab, alirocumab, altumomab, amatuximab, anatumomab mafenatox, anrukinzumab, apolizumab, arcitumomab, aselizumab, altinumab, atlizumab, atorolimiumab, tocilizumab, bapineuzumab, basiliximab, bavituximab, bectumomab, belimumab, benralizumab, bertilimumab, besilesomab, bevacizumab, bezlotoxumab, biciromab, bivatuzumab, bivatuzumab mertansine, blinatumomab, blosozumab, brentuximab vedotin, briakinumab, brodalumab, canakinumab, cantuzumab mertansine, cantuzumab mertansine, caplacizumab, capromab pendetide, carlumab, catumaxomab, cc49, cedelizumab, certolizumab pegol, cetuximab, citatuzumab bogatox, cixutumumab, clazakizumab, clenoliximab, clivatuzumab tetraxetan, conatumumab, crenezumab, cr6261, dacetuzumab, daclizumab, dalotuzumab, daratumumab, demcizumab, denosumab, detumomab, dorlimomab aritox, drozitumab, duligotumab, dupilumab, ecromeximab, eculizumab, edobacomab, edrecolomab, efalizumab, efungumab, elotuzumab, elsilimomab, enavatuzumab, enlimomab pegol, enokizumab, enoticumab, ensituximab, epitumomab cituxetan, epratuzumab, erenumab, erlizumab, ertumaxomab, etaracizumab, etrolizumab, evolocumab, exbivirumab, fanolesomab, faralimomab, farletuzumab, fasinumab, fbta05, felvizumab, fezakinumab, ficlatuzumab, figitumumab, flanvotumab, fontolizumab, foralumab, foravirumab, fresolimumab, fulranumab, futuximab, galiximab, ganitumab, gantenerumab, gavilimomab, gemtuzumab ozogamicin, gevokizumab, girentuximab, glembatumumab vedotin, golimumab, gomiliximab, gs6624, ibalizumab, ibritumomab tiuxetan, icrucumab, igovomab, imciromab, imgatuzumab, inclacumab, indatuximab ravtansine, infliximab, intetumumab, inolimomab, inotuzumab ozogamicin, ipilimumab, iratumumab, itolizumab, ixekizumab, keliximab, labetuzumab, lebrikizumab, lemalesomab, lerdelimumab, lexatumumab, libivirumab, ligelizumab, lintuzumab, lirilumab, lorvotuzumab mertansine, lucatumumab, lumiliximab, mapatumumab, maslimomab, mavrilimumab, matuzumab, mepolizumab, metelimumab, milatuzumab, minretumomab, mitumomab, mogamulizumab, morolimumab, motavizumab, moxetumomab pasudotox, muromonab-cd3, nacolomab tafenatox, namilumab, naptumomab estafenatox, narnatumab, natalizumab, nebacumab, necitumumab, nerelimomab, nesvacumab, nimotuzumab, nivolumab, nofetumomab merpentan, ocaratuzumab, ocrelizumab, odulimomab, ofatumumab, olaratumab, olokizumab, omalizumab, onartuzumab, oportuzumab monatox, oregovomab, orticumab, otelixizumab, oxelumab, ozanezumab, ozoralizumab, pagibaximab, palivizumab, panitumumab, panobacumab, parsatuzumab, pascolizumab, pateclizumab, patritumab, pemtumomab, perakizumab, pertuzumab, pexelizumab, pidilizumab, pintumomab, placulumab, ponezumab, priliximab, pritumumab, PRO 140, quilizumab, racotumomab, radretumab, rafivirumab, ramucirumab, ranibizumab, raxibacumab, regavirumab, reslizumab, rilotumumab, rituximab, robatumumab, roledumab, romosozumab, rontalizumab, rovelizumab, ruplizumab, samalizumab, sarilumab, satumomab pendetide, secukinumab, sevirumab, sibrotuzumab, sifalimumab, siltuximab, simtuzumab, siplizumab, sirukumab, solanezumab, solitomab, sonepcizumab, sontuzumab, stamulumab, sulesomab, suvizumab, tabalumab, tacatuzumab tetraxetan, tadocizumab, talizumab, tanezumab, taplitumomab paptox, tefibazumab, telimomab aritox, tenatumomab, tefibazumab, teneliximab, teplizumab, teprotumumab, tezepelumab, TGN1412, tremelimumab, ticilimumab, tildrakizumab, tigatuzumab, TNX-650, tocilizumab, toralizumab, tositumomab, tralokinumab, trastuzumab, TRBS07, tregalizumab, tucotuzumab celmoleukin, tuvirumab, ublituximab, urelumab, urtoxazumab, ustekinumab, vapaliximab, vatelizumab, vedolizumab, veltuzumab, vepalimomab, vesencumab, visilizumab, volociximab, vorsetuzumab mafodotin, votumumab, zalutumumab, zanolimumab, zatuximab, ziralimumab, zolimomab aritox, a glycoprotein, CD polypeptide, a HER receptor polypeptide, a cell adhesion polypeptide, a growth factor polypeptide, an insulin polypeptide, an insulin-related polypeptide, a coagulation polypeptide, a coagulation-related polypeptide, albumin, IgE, a blood group antigen, a colony stimulating factor, a receptor, a neurotrophic factor, an interferon, an interleukin, a viral antigen, a lipoprotein, calcitonin, glucagon, atrial natriuretic factor, lung surfactant, tumor necrosis factor-alpha and -beta, enkephalinase, mouse gonadotropin-associated peptide, DNAse, inhibin, activing, an integrin, protein A, protein D, a rheumatoid factor, an immunotoxin, a bone morphogenetic protein, a superoxide dismutase, a surface membrane polypeptide, a decay accelerating factor, an AIDS envelope, a transport polypeptide, a homing receptor, an addressin, a regulatory polypeptide, an immunoadhesin, a myostatin, a TALL polypeptide, an amyloid polypeptide, a thymic stromal lymphopoietin, a RANK ligand, a c-kit polypeptide, a TNF receptor, and an angiopoietin, the antibodies shown in Table 7 and biologically active fragments, analogs or variants thereof.

32. The method of claim 30, wherein the therapeutic polypeptide is a bi-specific T-cell engager molecule.

* * * * *